United States Patent [19]

Kamboj et al.

[11] Patent Number: 6,018,023
[45] Date of Patent: Jan. 25, 2000

[54] KAINATE-BINDING, HUMAN CNS RECEPTORS OF THE EAA3 FAMILY

[75] Inventors: Rajender Kamboj, Mississauga; Candace E. Elliott; Stephen L. Nutt, both of Etobicoke, all of Canada

[73] Assignee: Allelix Biopharmaceuticals Inc., Ontario, Canada

[21] Appl. No.: 08/487,691

[22] Filed: Jun. 7, 1995

Related U.S. Application Data

[63] Continuation of application No. 08/405,392, Mar. 15, 1995, Pat. No. 5,547,855, which is a continuation of application No. 07/989,793, Dec. 11, 1992, abandoned.

[51] Int. Cl.[7] .................................................. C07K 14/705
[52] U.S. Cl. .................... 530/350; 530/300; 530/395; 424/185.1; 536/23.5
[58] Field of Search ............................ 530/388.24, 350, 530/395, 300; 536/23.5; 435/69.1, 172.3; 562/573; 424/185.1

[56] References Cited

U.S. PATENT DOCUMENTS

| 5,202,257 | 4/1993 | Heinemann et al. ................. 435/252.3 |
| 5,547,855 | 8/1996 | Kamboj et al. ........................ 435/69.1 |

FOREIGN PATENT DOCUMENTS

| 0 529 994 | 3/1993 | European Pat. Off. . |
| 0 529 995 | 3/1993 | European Pat. Off. . |
| WO 91/06648 | 5/1991 | WIPO . |

OTHER PUBLICATIONS

Schulz et al., Principles of Protein Chemistry, Springer–Verlag:New York, pp. 14–16, 1979.
Strader et al., Structural basis of beta–adrenergic receptor function, FASEB J., 3: 1825–1832, 1989.
Sommer et al., A glutamate receptor channel with high affinity for domoate and kainate, EMBO J., 11(4): 1651–1656, Apr. 1992.
McNamara et al., Chromosomal localization of human glutamate receptor genes, J. Neurosci., 12(7): 2555–2562, Jul. 1992.
Paschen et al., RNA editing of the glutamate receptor subunits GluR2 and GluR6 in human brain tissue, J. Neurosci., 63: 1596–1602, 1994.
Stites et al., Basic and Clinical Immunology, Appleton & Lange:Norwalk, CT, pp. 52, 53, and 69, 1994.
Nutt et al., Neuroreport, 5(18):2625–9. (Abstract), Dec. 1994.
Better et al. (1992) Neuron 8: 257–264 Cloning of a Putative Glutamate Receptor: A Low Affinity Kainate–Binding Subunit.
Egebjerg et al. (1991) Nature 351: 745–748 "Cloning of a cDNA for a glutamate receptor subunit activated by kainate but not AMPA".
Eshhar et al. (1992) FEBS 297: 257–262 "Structural characterization and expression of a brain specific gene encoding chick kainate binding protein".
Gregor et al. (1989) Nature 342: 689–692 "Molecular structure of the chick cerebellar kainate–binding subunit of a putative glutamate receptor".
Oksenberg et al. (1992) Nature 360: 161–163 "A single amino–acid difference confers major pharmacological variation between human and rodent $5-HT_{1B}$ receptors".
Sakimura et al. (1992) Neuron 8: 267–274 "Primary Structure and Expression of the 2 Subumit of the Glutamate Receptor Channel Selective for Kainate".
Wada et al. (1989) Nature 342: 684–689 "Sequence and expression of a frog brain complementary DNA encoding a kainate–binding protein".
Werner et al. (1991) Nature 351: 742–744 "Cloning of a putative high–affinity kainate receptor expressed predominantly in hippocampal CA3 cells".
Carmie Puckett, et al., "Molecular cloning and chromosomal localization of one of the human glutamate receptor genes"; Proc. Natl. Acad. Sci. USA, vol. 88, pp. 7557–7561, Sep. 1991.
Sun et al., "Molecular Cloning, Chromosomal Mapping, and Functional Expression of Human Brain Glutamate Receptors," Proc. Natl. Acad. Sci., vol. 89, pp. 1443–1447 (Feb. 1992).
Bettler, B. et al. (1990) Neuron 5:383–95.
Sambrook, J., et al. (1989) Molecular Cloning: a laboratory manual, Cold Spring Harbor Press, Chapter 11 (selected pages included).
Jones et al. (1990), Blood 76(1):31–35.
Galizzi et al. (1990), Internat. Immunol. 2(7):669–675.

Primary Examiner—Lila Feisee
Assistant Examiner—Claire M. Kaufman
Attorney, Agent, or Firm—Foley & Lardner

[57] ABSTRACT

Neurotransmission by excitatory amino acids (EAAs) such as glutamate is mediated via membrane-bound surface receptors. DNA coding for one family of the kainate-binding type of EAA receptor, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

12 Claims, 16 Drawing Sheets

FIG. 1A

```
     EcoRI
      |
  1  GAATTCCGTCTCTTCTTTCCCCCTTTCCCTCTGTCTGTGCCTATCCCCCGACTTTTGC    60
     ----+----|----+----|----+----|----+----|----+----|----+----|
     CTTAAGGCAGAAGAAAGGGGGAAAGGGAGACAGACACGGATAGGGGGCTGAAAACG

61  ATCTGACCAAAGGACGAATGAGGGAGACGTTCCTGCAGATCGGGGCAGCAACTTTCCTCA   120
     ----+----|----+----|----+----|----+----|----+----|----+----|
     TAGACTGGTTTCCTGCTTACTCCCTCTGCAAGGACGTCTAGCCCCGTCGTTGAAAGGAGT

121  GCTGGTCTCTGGCTCCGGAGCTCAGAGAGCCGCTGATCCTCCGCGTCTGCGGCCCATGAAG   180
     ----+----|----+----|----+----|----+----|----+----|----+----|
     CGACCAGAGACCCGAGGCCTCGAGCAGCTAGGAGGCGCAGACGCCGGGTACTTC

181  AGAGAGAGAGCCGTGATGGGCTAGCGACAGCACTGAGGAGCCCCGAGAGAGCTCAGCCTT   240
     ----+----|----+----|----+----|----+----|----+----|----+----|
     TCTCTCTCTCGGCACTACCCGATCGCTGTCGTGACTCCTCGGGGCTCTCCGAGTCGGAA

241  GCCAGCCAGCTCCGCGGTCCCCACGCGGTTCCCCTCCGAGCTCGCTCCGTGGGAGCGCGCA   300
     ----+----|----+----|----+----|----+----|----+----|----+----|
     CGGTCGGTCGAGGCGCCAGGGTGCGCCAAGGGAGCGCGAGGCACCCCCTCGCGCGT

301  GCGTGCTTGGAACCGGAGCATCCAGAGAGGATGAGGCGGGACCCGGCCCAAGTTGGGTG   360
     ----+----|----+----|----+----|----+----|----+----|----+----|
     CGCACGAACCTTGGCCTCGTAGGTCTCTCCTACTCCGCCCCCTGGGCCGGGTTCAACCCAC

361  CATCTCTCGGGCGTCCGGCAGCGGTCTGTATCTCGGCATGAATTAAGAAGCTAGGAAGATG   420
     ----+----|----+----|----+----|----+----|----+----|----+----|
     GTAGAGAGCCCCGCAGCGCCGGCAGCGCTGGCTTAATTCTTCGATCCTTCTAC    -30
                                          M
```

FIG. 1B

```
421  GAGCACGGCACACTCCTCGCCCAGCCAGGGCTCTGGACCCAGGAGACACCAGCTGGGCACTC
     ----+----+----+----+----+----+----+----+----+----+----+----+  480
     CTCGTGCCGTGTGAGGAGCGGGTCGGCCCGAGACCTGGTCCCTGTGTGGTCGACCCGTGAG
-29  E  H  G  T  L  L  A  Q  P  G  L  W  T  R  D  T  S  W  A  L    -10
                                              |_ Mature Amino-Terminal 481  CTCTATTTCCTCTGCTATATCCCCTCAGACCGCCCCGCCCAAGTACTCAGGATCGGAGGG
     ----+----+----+----+----+----+----+----+----+----+----+----+  540
     GAGATAAAGGAGACGATATAGGAGGAGTCTGGCGGGGCGTTCATGAGTCCTAGCCTCCC
-09  L  Y  F  L  C  Y  I  L  P  Q  T  A  P  Q  V  L  R  I  G  G    11

541  ATTTTTGAAACAGTGGAAAATGAGCCTGTTAATGTTGAAGAATTAGCTTTCAAGTTTGCA
     ----+----+----+----+----+----+----+----+----+----+----+----+  600
     TAAAAACTTTGTCACCTTTTACTCGGACAATTACAACTTCTTAATCGAAAGTTCAAACGT
 12  I  F  E  T  V  E  N  E  P  V  N  V  E  E  L  A  F  K  F  A    31

601  GTCACCAGCATTAACAGAAACAGAAACCCTGATGCCTAACACCACATTAACCTATGACATC
     ----+----+----+----+----+----+----+----+----+----+----+----+  660
     CAGTGGTCGTAATTGTCTTTGCTTGGACTACGGATTGTGGTGTAATTGGATACTGTAG
 32  V  T  S  I  N  R  N  R  T  L  M  P  N  T  T  L  T  Y  D  I    51

661  CAGAGAATTAACCTTTTTGATAGTTTTGAAGCCTCGCGGAGAGCATGACCAGCTGGCT
     ----+----+----+----+----+----+----+----+----+----+----+----+  720
     GTCTCTTAATTGGAAAAACTATCAAAACTTCGGAGCGCCTCTCGTACACTGGTCGACCGA
 52  Q  R  I  N  L  F  D  S  F  E  A  S  R  R  A  C  D  Q  L  A    71

721  CTTGGTGTGGCTGCTCTCTTTGGCCCTTCCCATAGTCCTCCGTCAGTGCTGTGCAGTCT
     ----+----+----+----+----+----+----+----+----+----+----+----+  780
     GAACCACACCGACGAGAGAAACCGGAAGGTATCGAGGAGCAGTCACGACACGTCAGA
 72  L  G  V  A  A  L  F  G  P  S  H  S  S  S  V  S  A  V  Q  S    91
```

FIG. IC

```
781  ATTTGCAATGCTCTCGAAGTTCCACACATACAGACCCGCTGGAAACACCCCTCGGTGGAC   840
     ------+---------+---------+---------+---------+---------+
     TAAACGTTACGAGAGCTTCAAGGTGTGTATGTCTGGGCGACCTTGTGGGAGCCACCTG
92   I  C  N  A  L  E  V  P  H  I  Q  T  R  W  K  H  P  S  V  D   111

841  AACAAAGATTTGTTTTACATCAACCTTTACCCAGATTATGCAGCTATCAGCAGGGCGATC   900
     ------+---------+---------+---------+---------+---------+
     TTGTTTCTAAACAAAATGTAGTTGGAAATGGGTCTAATACGTCGATAGTCGTCCCGCTAG
112  N  K  D  L  F  Y  I  N  L  Y  P  D  Y  A  A  I  S  R  A  I   130

901  CTGGATCTGGTCCCTCTATTACAACTGGAAAACAGTGACAGTGGTGTATGAAGACAGCACA   960
     ------+---------+---------+---------+---------+---------+
     GACCTAGACCAGGAGATAATGTTGACCTTTTGTCACTGTCACCACATACTTCTGTCGTGT
132  L  D  L  V  L  Y  Y  N  W  K  T  V  T  V  Y  E  D  S  T    150

961  GGTCTAATTCGTCTACAAGAGCTCATCAAAGCTCCCTCCAGATATATTAAAATCAAA     1020
     ------+---------+---------+---------+---------+---------+
     CCAGATTAAGCAGATGTTCTCGAGTAGTTCGAGGGAGTCTATATTATAATTTTAGTTT
152  G  L  I  R  L  Q  E  L  I  K  A  P  S  R  Y  N  I  K  I  K   170

1021 ATCCGCCAGCTGCCCTCTGGGAATAAAGATGCCAAGCCTTTACTCAAGGAGATGAAGAAA   1080
     ------+---------+---------+---------+---------+---------+
     TAGGCGGTCGACGGGAGACCCTTATTTCTACGGTTCGGAAATGAGTTCCTCTACTTCTTT
172  I  R  Q  L  P  S  G  N  K  D  A  K  P  L  L  K  E  M  K  K   190

1081 GGCAAGGAGTTCTATGTGATATTGATTGTTCACATGAAACAGCCGCTGAAATCCTTAAG   1140
     ------+---------+---------+---------+---------+---------+
     CCGTTCCTCAAGATACACTATAAACTAACAAGTGTACTTTGTCGGCGACTTTAGGAATTC
192  G  K  E  F  Y  V  I  F  D  C  S  H  E  T  A  A  E  I  L  K   211
```

FIG. 1D

```
1141  CAGATTCTGTTCATGGGCATGATGACCGAATACTATCACTACTTTTTCACAACCCTGGAC
      ------+---------+---------+---------+---------+---------+  1200
      GTCTAAGACAAGTACCCGTACTACTGGCTTATGATAGTGATGAAAAAGTGTTGGGACCTG
212    Q  I  L  F  M  G  M  M  T  E  Y  Y  H  Y  F  F  T  T  L  D   231

1201  TTATTTGCTTTGGATCTGGAACTCTATAGGTACAGTGGCGTAAACATGACCGGGTTTGGG
      ------+---------+---------+---------+---------+---------+  1260
      AATAAACGAAACCTAGACCTTGAGATATCCATGTCACCGCATTTGTACTGGCCCAAACCC
232    L  F  A  L  D  L  E  L  Y  R  Y  S  G  V  N  M  T  G  F  G   251

1261  CTGCTTAACATTGACAACCCTCACGTGTCATCCATCATTGAGAAGTGGTCCATGGAGAGA
      ------+---------+---------+---------+---------+---------+  1320
      GACGAATTGTAACTGTTGGGAGTGCACAGTAGTAACTCTTCACCAGGTACCTCTCT
252    L  L  N  I  D  N  P  H  V  S  S  I  I  E  K  W  S  M  E  R   271

1321  CTGCAGGCCCCCACCCCAGGCCCCGAGACTGGCCTTTTGGATGGCATGATGACAACTGAAGCG
      ------+---------+---------+---------+---------+---------+  1380
      GACGTCCGGGGGTGGGTCCGGGGCTCTGACCGGAAAACCTACCGTACTACTGTTGACTTCGC
272    L  Q  A  P  P  R  P  E  T  G  L  L  D  G  M  M  T  T  E  A   291

1381  GCTCTCGATGTACGATGCTGTGTACATGGTGGCCATTGCCTCGCACCGGGCATCCCAGCTG
      ------+---------+---------+---------+---------+---------+  1440
      CGAGACTACATGCTACGACACATGTACCACCGGTAACGGAGCGTGGCCGGTAGGGTCGAC
292    A  L  M  Y  D  A  V  Y  M  V  A  I  A  S  H  R  A  S  Q  L   311

1441  ACCGTCAGCTCCCTGCAGTGCCATAGACATAAGCCATGGCCTCGGACCCAGATTTATG
      ------+---------+---------+---------+---------+---------+  1500
      TGGCAGTCGAGGACGTCACGGTATCTGTATTCGTACCGCGGAGCCTGGGTCTAAATAC
312    T  V  S  S  L  Q  C  H  R  H  K  P  W  R  L  G  P  R  F  M   331
```

FIG. 1E

```
1501  AACCTGATCAAAGAGGCCCGGTGGGATGGCTTGACTGGGCATATCACCTTTAATAAACC  1560
      ----+----+----+----+----+----+----+----+----+----+----+----+
      TTGGACTAGTTTCTCCGGGCCACCCTACCGAACTGACCCGTATAGTGGAAATTATTTTGG
332   N  L  I  K  E  A  R  W  D  G  L  T  G  H  I  T  F  N  K  T  351

1561  AATGGCTTGAGGAAGGATTTGATCTGGACATTATTAGTCTCAAAGAGGAAGAACTGAA   1620
      ----+----+----+----+----+----+----+----+----+----+----+----+
      TTACCGAACTCCTTCCTAAAACTAGACCTGTAATAATCAGAGTTTCTCCTTCCTTGACTT
352   N  G  L  R  K  D  F  D  L  D  I  I  S  L  K  E  E  G  T  E  371

1621  AAGATTGGGATTTGGAATTCCAACAGTGGGCTTAACATGACGGACAGCAACAAAGACAAG  1680
      ----+----+----+----+----+----+----+----+----+----+----+----+
      TTCTAACCCTAAACCTTAAGTTGTCACCCGAATTGTACTGCCTGTCGTTGTTTCTGTTC
372   K  I  G  I  W  N  S  N  S  G  L  N  M  T  D  S  N  K  D  K  391

1681  TCCAGCAATATCACTGATTCATTGGCCAACAGAACACTCATTGTCACCACCATTCTGGAA  1740
      ----+----+----+----+----+----+----+----+----+----+----+----+
      AGGTCGTTATAGTGACTAAGTAACCGGTTGTCTTGTGAGTAACAGTGGTGGTAAGACCTT
392   S  S  N  I  T  D  S  L  A  N  R  T  L  I  V  T  T  I  L  E  411

1741  GAACCCTATGTTATGTACAGGAAATCTGATAAGCCTCTATATGAAATGACAGATTTGAA   1800
      ----+----+----+----+----+----+----+----+----+----+----+----+
      CTTGGGATACAATACATGTCCTTTAGACTATTCGGAGATATACTTTACTGTCTAAACTT
412   E  P  Y  V  M  Y  R  K  S  D  K  P  L  Y  G  N  D  R  F  E  431

1801  GGATATATTGCCTAGACCTGTGTTGAAAGAATTGTCAAACATCCTGGGTTTCATTTATGATGTT  1860
      ----+----+----+----+----+----+----+----+----+----+----+----+
      CCTATAACGGATCTGGACAACTTTCTTAACAGTTTGTAGGACCCAAAGTAAATACTACAA
432   G  Y  C  L  D  L  L  K  E  L  S  N  I  L  G  F  I  Y  D  V  451
```

FIG. 1F

```
1861  AAACTAGTTCCGATGGCAAATATGGGGCCCAGAATGACAAAGGGGAGTGAAGGGATG
      ----+----+----+----+----+----+----+----+----+----+----+----+  1920
      TTTGATCAAGGGCTACCGTTTATACCCCGGGTCTTACTGTTTCCCCTCACCTTGCCCTAC
452   K  L  V  P  D  G  K  Y  G  A  Q  N  D  K  G  E  W  N  G  M   471

1921  GTTAAAGAACTCATAGATCACAGGGCTGACCTGGCAGTGCTCCTCTTACCATCACCTAC
      ----+----+----+----+----+----+----+----+----+----+----+----+  1980
      CAATTTCTTGAGTATCTAGTGTCCCGACTGGACCGTCACGGAGGAGAATGGTAGTGGATG
472   V  K  E  L  I  D  H  R  A  D  L  A  V  A  P  L  T  I  T  Y   491

1981  GTGCGGGAGAAAGTCATTGACTTCTCCAAACCCTTCATGACCCTAGGCATCAGCATTCTC
      ----+----+----+----+----+----+----+----+----+----+----+----+  2040
      CACGCCCTCTTTCAGTAACTGAAGAGGTTTGGGAAGTACTGGGATCCGTAGTCGTAAGAG
492   V  R  E  K  V  I  D  F  S  K  P  F  M  T  L  G  I  S  I  L   511

2041  TACCGGAAGCCCAATGGTACCAATCCAGGCGTTTTCTTCCTCAACCCCCTGTCTCCA
      ----+----+----+----+----+----+----+----+----+----+----+----+  2100
      ATGGCCTTCGGGTTACCATGGTTAGGTCCGCAAAAGAGGAGTTGGGGACAGAGGT
512   Y  R  K  P  N  G  T  N  P  G  V  F  S  F  L  N  P  L  S  P   531

2101  GATATATTGGATGTATGTGCTCTTAGCCTGTGTCAGCTGGAGTCAGCTGTGTACTCTTTGTGATT
      ----+----+----+----+----+----+----+----+----+----+----+----+  2160
      CTATAAACCTACATACACGAGAATCGGACGACAACCCTCAGTCGACACATGAGAAACACTAA
532   D  I  W  M  Y  V  L  L  A  C  L  G  V  S  C  V  L  F  V  I   551

2161  GCAAGGTTTACACCCTACGAGTGGTATAACCCCACCCATGCAACCCTGACTCAGACGTg
      ----+----+----+----+----+----+----+----+----+----+----+----+  2220
      CGTTCCAAATGTGGGATGCTCACCATATTGGGGGTGGGTACGTTGGGACTGAGTCTGCAc
552   A  R  F  T  P  Y  E  W  Y  N  P  H  P  C  N  P  D  S  D  V   571
```

FIG. IG

```
2221 GTGGAAACAATTTACTTTACTAAATAGTTTCTGGTTTGGAGTTGGAGCTCTCATGCAG 2280
     ---------+---------+---------+---------+---------+---------+
     CACCTTTGTTAAAATGAAATGATTTATCAAGACCAAACCTCAACCTCGAGAGTACGTC
572  V  E  N  N  F  T  L  L  N  S  F  W  F  G  V  G  A  L  M  Q  591

2281 CAAGGATCAGAGCTGATGCCCAAAGCTCTATCGACCAGAATAGTTGGAGGGATATGGTGG 2340
     ---------+---------+---------+---------+---------+---------+
     GTTCCTAGTCTCGACTACGGGTTTCGAGATAGCTGGTCTTATCAACCTCCCTATACCACC
592  Q  G  S  E  L  M  P  K  A  L  S  T  R  I  V  G  G  I  W  W  611

2341 TTTTTCACCCTAATCATCATTTCATCCTACACGGCCAATCTGGCTGCCTTCTTGACAGTA 2400
     ---------+---------+---------+---------+---------+---------+
     AAAAAGTGGGATTAGTAGTAAAGTAGGATGTGCCGGTTAGACCGACGGAAGAACTGTCAT
612  F  F  T  L  I  I  I  S  S  Y  T  A  N  L  A  A  F  L  T  V  631

2401 GAGAGAAATGGAATCCCCCATAGATTCGGCAGATGATCTGGCAAAGCAAACCAAGATAGAA 2460
     ---------+---------+---------+---------+---------+---------+
     CTCTCTTACCTTAGGGGTATCTAAGCCGTCTACTAGACCGTTTCGTTTGGTTCTATCTT
632  E  R  M  E  S  P  I  D  S  A  D  D  L  A  K  Q  T  K  I  E  651

2461 TATGGGGCGGTTAGAGATGGATCAACAATGACCTTCTTCAAGAAATCAAAAATCTCCACC 2520
     ---------+---------+---------+---------+---------+---------+
     ATACCCCGCCAATCTCTACCTAGTGTTACTGGAAGAAGTTCTTTAGTTTTTAGAGGTGG
652  Y  G  A  V  R  D  G  S  T  M  T  F  F  K  K  S  K  I  S  T  671

2521 TATGAGAAGATGTGGGCTTTCATGAGCAGCAGGCAGCAGCGCCCTGGTAAGAAACAGT 2580
     ---------+---------+---------+---------+---------+---------+
     ATACTCTTCTACACCCGAAAGTACTCGTCGTCCGTCGTCGGCGGGACCATTCTTTGTCA
672  Y  E  K  M  W  A  F  M  S  S  R  Q  Q  T  A  L  V  R  N  S  691
```

FIG. 1H

```
2581  GATGAGGGGATCCAGAGAGTGCTCACCACAGACTACGCGCTGCTGATGGAGTCCACCAGC  2640
      ----+----+----+----+----+----+----+----+----+----+----+----+
      CTACTCCCCTAGGTCTCTCACGAGTGGTGTCTGATGCGCGACGACTACCTCAGGTGGTCG
 692  D  E  G  I  Q  R  V  L  T  T  D  Y  A  L  L  M  E  S  T  S   711

2641  ATTGAGTATGTGACGCAGAGAAACTGCAACCTCACTCAGATCGGGGGCCTCATTGACTCC  2700
      ----+----+----+----+----+----+----+----+----+----+----+----+
      TAACTCATACACTGCGTCTCTTTGACGTTGGAGTGAGTCTAGCCCCCGGAGTAACTGAGG
 712  I  E  Y  V  T  Q  R  N  C  N  L  T  Q  I  G  G  L  I  D  S   731

2701  AAAGGTTACGGAGTGGGAACACCTATTGGTTCTCCTTACCGGGATAAAATTACTATTGCT  2760
      ----+----+----+----+----+----+----+----+----+----+----+----+
      TTTCCAATGCCTCACCCTTGTGGATAACCAAGAGGAATGGCCCTATTTTAATGATAACGA
 732  K  G  Y  G  V  G  T  P  I  G  S  P  Y  R  D  K  I  T  I  A   751

2761  ATTCTTCAACTCCAAGAAGAAGGAAGCTGCATATGATGAAAGAGAAGTGGTGGCGTGGG  2820
      ----+----+----+----+----+----+----+----+----+----+----+----+
      TAAGAAGTTGAGGTTCTTCTTCCCTTCGACGTATACTACTTTCTCTTCACCACCGCACCC
 752  I  L  Q  L  Q  E  E  G  K  L  H  M  M  K  E  K  W  W  R  G   771

2821  AATGGCTGCCCCGAGGAAGACAACAAAGAAGCCAGTGCCCTGGGAGTGGAAAATATTGGA  2880
      ----+----+----+----+----+----+----+----+----+----+----+----+
      TTACCGACGGGGCTCCTTCTGTTGTTTCTTCGGTCACGGGACCCTCACCTTTTATAACCT
 772  N  G  C  P  E  E  D  N  K  E  A  S  A  L  G  V  E  N  I  G   791

2881  GGCATCTTCATTGTTCTGGCTGCCGGACTGGTCCTTTCTGTATTTGTAGCTATTGGAGAA  2940
      ----+----+----+----+----+----+----+----+----+----+----+----+
      CCGTAGAAGTAACAAGACCGACGGCCTGACCAGGAAAGACATAAACATCGATAACCTCTT
 792  G  I  F  I  V  L  A  A  G  L  V  L  S  V  F  V  A  I  G  E   811
```

FIG. 11

```
2941 TTCATATACAAATCACGGAAGAATAATGATATTGAACAGTGTCTCTCTTTCAACGCTATC 3000
     ----------+---------+---------+---------+---------+---------+
     AAGTATATGTTTAGTGCCTTCTTATTACTATAACTTGTCACAGAGAGAAAGTTGCGATAG
812   F  I  Y  K  S  R  K  N  N  D  I  E  Q  C  L  S  F  N  A  I  831

3001 ATGGAAGAACTGGGAATCTCACTGAAGAATCAGAAAAATAAGAAAAAGTCAAGAACT 3060
     ----------+---------+---------+---------+---------+---------+
     TACCTTCTTGACCCTTAGAGTGACTTCTTAGTCTTTTTATTCTTTTTCAGTTCTTGA
832   M  E  E  L  G  I  S  L  K  N  Q  K  K  I  K  K  K  S  R  T  851

3061 AAGGGGAAATCTTCCTTCACAAGTATCCTTACTTGTCATCAGAGACGAACTCAGAGAAAA 3120
     ----------+---------+---------+---------+---------+---------+
     TTCCCCTTTAGAAGGAAGTGTTCATAGGAATGAACAGTAGTCTCTGCTTGAGTCTCTTTT
852   K  G  K  S  S  F  T  S  I  L  T  C  H  Q  R  R  T  Q  R  K  871

3121 GAGACTGTGGCGTGATCCAAGGAAACGCCTGTAGGAAGAAAAAGGATGCATTCCCTACAG 3180
     ----------+---------+---------+---------+---------+---------+
     CTCTGACACCGCACTAGGTTCCTTTGCGGACATCCTTCTTTTTCCTACGTAAGGGATGTC
872   E  T  V  A  875
```

FIG. 1J

```
3181  ATTTTTGGAGAAAGGATTTCTGAGGAGTTGTGTGATGTGTTTCCATATATCTATATCCAT
      ----:----+----:----+----:----+----:----+----:----+----:----+  3240
      TAAAAACCTCTTTCCTAAAGACTCCTCAACACACTACACAAGGTATATAGATATAGGTA

3241  AACTCTGATTATGAATACAGAGAATACAAAAGTTAAAAAGCTCACATAGATAT
      ----:----+----:----+----:----+----:----+----:----+----:----+  3300
      TTGAGACTAATACTTATGTCTATATTCTTTATGTTTTCAAATTTTCGAGTGTATCTATA

3301  GACTTGGGAAGTGACACCAGTTCTTTTAAAATAAATTTGTATGCACAAAAAAAAAAAA
      ----:----+----:----+----:----+----:----+----:----+----:----+  3360
      CTGAACCCTTCACTGTGGTCAAGAAAATTTATTTAAACATACGTGTTTTTTTTTTTT

EcoRI
                                            |--|
3361  AAAAAAAAAAAAAAAAAAAGGAATTC   3385
      ----:----+----:----+----:--
      TTTTTTTTTTTTTTTTTTTCCTTAAG
```

FIG. 4A

AMINO ACID SEQUENCE:

```
HumEAA3b   626  AAFLTVERMESPINSADDLAKQTKIEYGAVRDGSTMTFFKKSKISTYEKM  675
                ||||||||||||||| |||||||||||||||||||||||||||||||||
HumEAA3a   626  AAFLTVERMESPIDSADDLAKQTKIEYGAVRDGSTMTFFKKSKISTYEKM  675
```

NUCEOTIDE SEQUENCE:

```
HumEAA3b   2402  GAGAGAATGGAATCCCCCATAAATTCGGCAGATGATCTGGCAAAGCAAAC  2451
                 |||||||||||||||||||||| |||||||||||||||||||||||||||
HumEAA3a   2402  GAGAGAATGGAATCCCCCATAGATTCGGCAGATGATCTGGCAAAGCAAAC  2451
```

FIG. 4B

AMINO ACID SEQUENCE:

```
HumEAA3c   798  AAGLVLSVFVAIGEFIYKSRKNNDIEQVSHLFLGLVSL*............  835
                ||||||||||||||||||||||||||||||| :   :  :
HumEAA3a   798  AAGLVLSVFVAIGEFIYKSRKNNDIEQCLSFNAIMEELGISLKNQKKIKK  847
```

NUCLEOTIDE SEQUENCE:

```
HumEAA3c   2950  CAAAATCACGGAAGAATAATGATATATTGAACAG......GTGAGTCATCTCTT  2994
                 |||||||||||||||||||||||||||||||||      |||   ||| ||
HumEAA3a   2950  CAAAATCACGGAAGAATAATGATATATTGAACAGTGTCTCTCTTTCAACGCTA  2999

HumEAA3c   2995  TCTAGGACTGGTTAGTTTATAGTTTGCATTATCTGTCTTAAGTTTGGGGG   3044
                 ||   |||                     ||
HumEAA3a   3000  TCATGGAAGAACTGGGAATCTCACTGAAGAATCAGAAAAAATAAAGAAA   3049

HumEAA3c   3045  TTTTTAAGGATGTTTGCTCTTTT   3069
                 |||   ||
HumEAA3a   3050  AAGTCAAGAACTAAGGGGAAATCT   3074
```

FIG. 4C

AMINO ACID SEQUENCE:

```
                |------ Signal Peptide ------||-- Mature Protein
                                              1
HumEAA3d   -30  MEHGTLLAQPGLWTRDTSWGLLYFLCYILPQTAPQ...................  5
                ||||||||||||||||||||||||||||||||||
HumEAA3a   -30  MEHGTLLAQPGLWTRDTSWGLLYFLCYILPQTAPQVLRIGGIFETVENEP 20

HumEAA3d     6  ..............................................VLRIACDQL 14
                                                                |||||||||
HumEAA3a    21  VNVEELAFKFAVTSINRNRTLMPNTTLTYDIQRINLFDSFEVLRIACDQL 70
```

NUCLEOTIDE SEQUENCE:

```
HumEAA3d   500  ATCCCTCCCTCAGAACCGCCCCGCAAGTACTCAGGATC............ 535
                ||||||||||||||||||||||||||||||||||||||
HumEAA3a   500  ATCCCTCCCTCAGAACCGCCCCGCAAGTACTCAGGATCGGAGGGATTTTGA 549

HumEAA3d   536  ....GCATGTGACCAGCTGGCTCTCTTTGGTGTGGCTGCTCTCTTTGGCCCTT 581
                    ||||||||||||||||||||||||||||||||||||||||||||||||
HumEAA3a   700  GAGAGCATGTGACCAGCTGGCTCTCTTTGGTGTGGCTGCTCTCTTTGGCCCTT 749
```

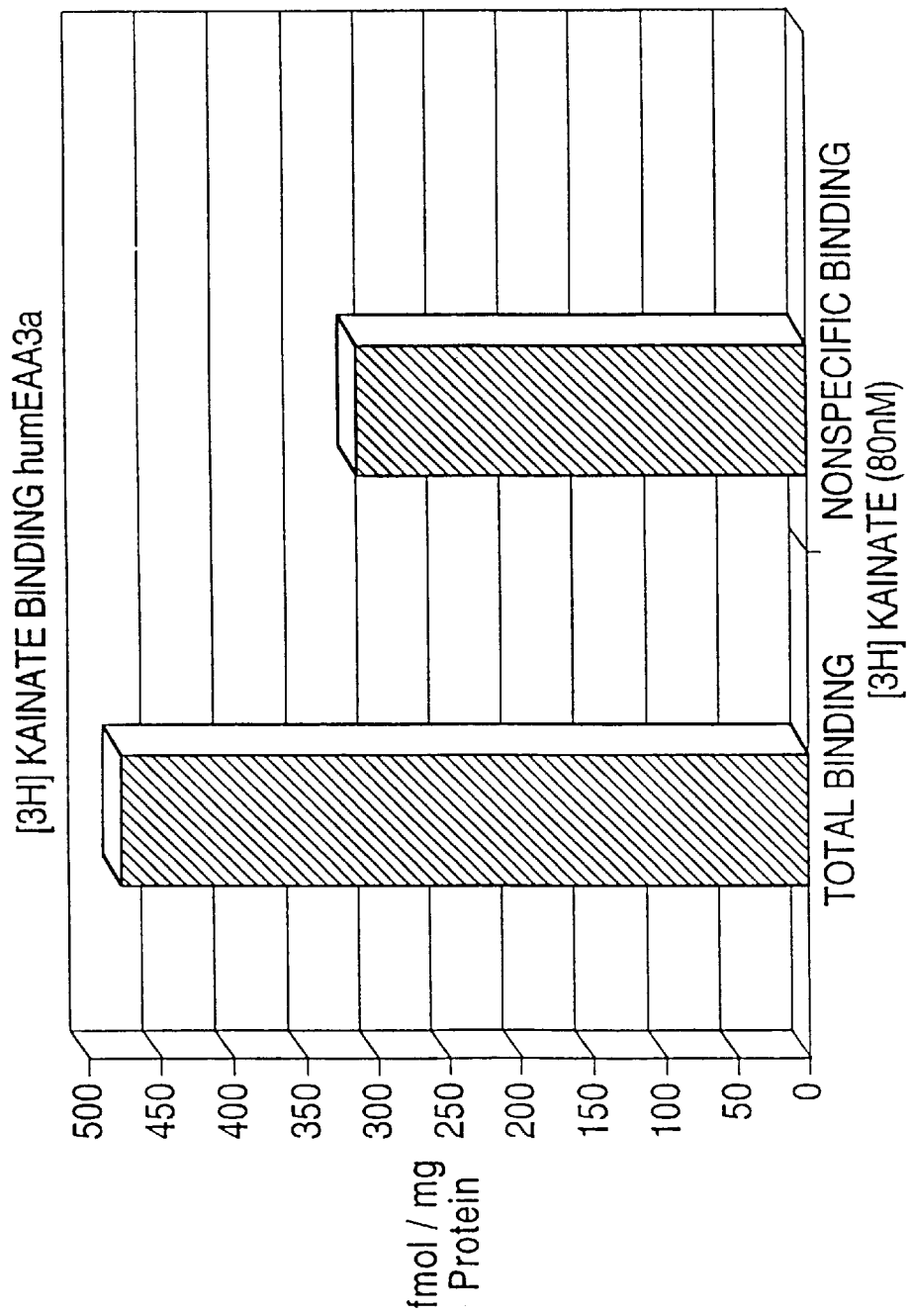

KAINATE-BINDING, HUMAN CNS RECEPTORS OF THE EAA3 FAMILY

This application is a continuation of application Ser. No. 08/405,392, filed Mar. 15, 1995, now U.S. Pat. No. 5,547,855, which is a continuation of Ser. No. 07/989,793, filed Dec. 11, 1992, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impulses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (α-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Non-human cDNAs which appear to encode the kainate-type of receptor have been reported. Egebjerg et al. (Nature 351: 745, 1991) and WO91/06648, each describe the isolation of a cDNA from rat called GluR6 which, although related by sequence to AMPA receptor genes, forms a receptor which is not activated by AMPA but rather by glutamate, quisqualate, and preferentially, kainate. Other kainate binding proteins, which do not readily exhibit ion channel properties when expressed in a homomeric fashion, have also been cloned from frog (Wada et al., Nature 342: 684, 1989), chicken (Gregor et al., Nature 342: 689, 1989; Eshar et al., FEBS Lett. 297: 257, 1992), mouse (Sakimura et al., Neuron 8: 267, 1992) and rat (Werner et al., Nature 351: 742, 1991; Bettler et al., Neuron 8; 257, 1992; Herb et al., Neuron 8: 775, 1992).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex.

In the search for therapeutics useful to treat CNS disorders in humans, it is highly desirable to obtain knowledge of human EAA receptors. A specific understanding of human receptors would provide a means to screen for compounds that react therewith, i.e. to stimulate or inhibit receptor activity, and thus, provides a means to identify compounds having potential therapeutic utility in humans. Non-human mammalian models are not suitable for this purpose despite significant receptor sequence homology as minute sequence differences between species homologues of the same receptor from different species can cause dramatic pharmacological variation (Oksenberg et al., Nature, 360: 161, 1992). It is therefore particularly desirable to provide cloned cDNA encoding human EAA receptors, and cell lines expressing these receptors in a homogeneous fashion, in order to generate a proper screening method for compounds therapeutically useful in humans. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Polynucleotides coding for a family of EAA receptors which in addition to binding glutamate with an affinity typical of EAA receptors, also exhibit ligand binding properties characteristic of kainate-type EAA receptors, have now been identified and characterized. A representative member of this human EAA receptor family is herein designated human EAA3a. Sequence-related polynucleotides coding for naturally occurring variants of the human EAA3a receptor have also been identified, and constitute additional members of this receptor family, herein referred to as the human EAA3 receptor family.

The present invention thus provides, in one of its aspects, an isolated polynucleotide, consisting either of DNA or of RNA, which codes for a human EAA3 receptor or for a kainate-binding fragment thereof.

In another aspect of the present invention, there is provided a cell that has been genetically engineered to produce a kainate-binding, human EAA receptor belonging to the herein-defined EAA3 family. In related aspects of the present invention, there are provided recombinant DNA constructs and relevant methods useful to create such cells.

In another aspect of the present invention, there is provided a method for evaluating interaction between a test ligand and a human EAA receptor, which comprises the steps of incubating the test ligand with a genetically engineered cell of the present invention, or with a membrane preparation derived therefrom, and then assessing said interaction by determining receptor/ligand binding.

Other aspects of the present invention, which encompass various applications of the discoveries herein described, will become apparent from the following detailed description, and from the accompanying drawings, in which:

BRIEF REFERENCE TO THE DRAWINGS

FIGS. 1A–1J provide the nucleotide sequence (SEQ ID NO:1) of a cDNA insert comprising DNA coding for an excitatory amino acid receptor of the present invention, and the deduced amino acid sequence (SEQ ID NO:2) thereof;

FIG. 4A shows the differences in the amino acid and nucleic acid sequences of the EAA3b receptor and the EAA3a receptor of FIGS. 1A–1J. The amino acid sequences of human EAAb and human EAAa and the nucleic acid sequences of human EAAb and human EAAa shown in this figure are referred to herein as, respectively, SEQ ID NOs: 3, 4, 5 and 6.

FIG. 4B shows the differences in the amino acid and nucleic acid sequences of the EAA3c receptor and the EAA3a receptor of FIGS. 1A–1J. The amino acid sequences of human EAAc and human EAAa and the nucleic acid sequences of human EAAc and human EAAa shown in this figure are referred to herein as, respectively, SEQ ID NOs: 7, 8, 9 and 10.

FIG. 4C shows the differences in the amino acid and nucleic acid sequences of the EAA3d receptor and the EAA3a receptor of FIGS. 1A–1J. The amino acid sequences of human EAAd and human EAAa and the nucleic acid sequences of human EAAd and human EAAa shown in this figure are listed herein as, respectively, SEQ ID NOs: 11, 12, 13 and 14.

FIG. 5 illustrates the ligand-binding property of an EAA receptor expressed from the coding region provided in FIGS. 1A–1J (SEQ ID NO:1).

DETAILED DESCRIPTION OF THE INVENTION AND ITS PREFERRED EMBODIMENTS

Figure 2:
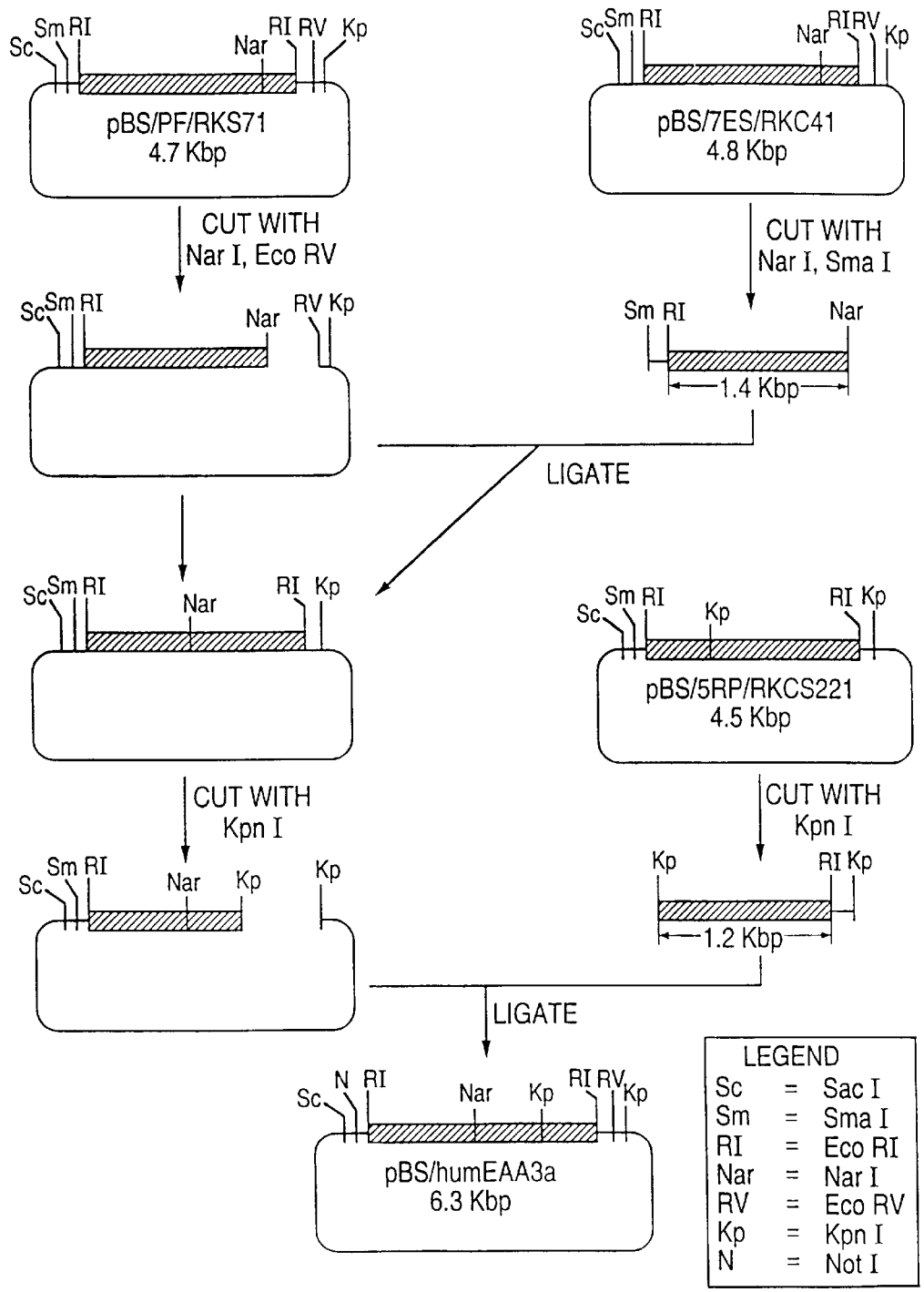
FIG. 2 illustrates with plasmid maps the strategy used to construct a vector harbouring the full-length DNA sequence illustrated in FIGS. 1A–1J (SEQ ID NO:1)

The invention relates to excitatory amino acid (EAA) receptors of human origin, and is directed more particularly to a novel family of kainate-type human EAA receptors, herein designated the human EAA3 receptor family. As used herein, the term "human EAA3 receptor" is intended to embrace the human EAA3a receptor, and kainate-binding variants of the EAA3a receptor that are structurally related thereto, i.e. share at least 97% amino acid identity including naturally occurring and synthetically derived variants of the EAA3a receptor. Naturally occurring variants of the human EAA3a receptor include particularly the receptors herein designated EAA3b, EAA3c and EAA3d. Synthetically derived variants of the human EAA3a receptor include kainate-binding variants that incorporate one or more, e.g. 1–56, amino acid deletions or additions relative to the EAA3a receptor, or one or more amino acid substitutions, e.g. 1–32 amino acid substitutions relative to the EAA3a receptor.

The term "kainate-binding", as it is used herein with respect to EAA3 receptors, and variants and fragments thereof, is meant to encompass those receptors, variants and fragments that display greater binding affinity for kainate than for either glutamate, AMPA or NMDA, as determined in assays of conventional design, such as the assays herein described.

Each of the naturally occurring members of the EAA3 receptor family possesses structural features characteristic of EAA receptors in general, including extracellular amino (N-) and carboxy-terminal (C-terminal) regions, as well as four internal hydrophobic domains which serve to anchor the receptor within the cell surface membrane. The particular human EAA receptor designated EAA3a is a protein characterized structurally as a single polypeptide chain that is produced initially in precursor form bearing a 30 residue N-terminal signal peptide, and is transported to the cell surface in mature form i.e. lacking the signal peptide and consisting of 875 amino acids arranged in the sequence illustrated, by single letter code, in FIGS. 1A–1J (SEQ ID NO:2). Unless otherwise stated, the term "EAA3 receptor" refers to the mature form of the receptor protein, and amino acid residues of EAA3 receptors are accordingly numbered with reference to the mature protein sequence. With respect to structural domains of the receptor, hydropathy analysis reveals four putative transmembrane domains, one spanning residues 533–552 inclusive (TM-1), another spanning residues 574–594 (TM-2), a third spanning residues 605–623 (TM-3) and the fourth spanning residues 790–810 (TM-4). Based on this assignment, it is likely that the human EAA3a receptor structure, in its natural membrane-bound form, consists of a 532 amino acid N-terminal extracellular domain, followed by a hydrophobic region containing the four transmembrane domains and an extracellular, 65 amino acid C-terminal domain.

As shown in FIGS. 4A–4C (and in SEQ ID NOS. 3–14), three structurally related variants of the EAA3a receptor, which occur naturally in human brain tissue, have also been identified and are herein designated the EAA3b, EAA3c and EAA3d receptors. As deduced from nucleotide sequences of the genes coding for them, the EAA3b variant shares greater than 99% amino acid identity with EAA3a, differing only by a single amino acid at position 639 which is an aspartate residue in the EAA3a receptor and an asparagine residue in the EAA3b receptor (FIG. 4A (SEQ ID NOS. 3–6)). The EAA3c receptor (SEQ ID NO:17), on the other hand, is a truncated version of EAA3a in which 40 amino acids have been eliminated from the C-terminus. Additionally, the last eleven amino acid residues at the C-terminus of EAA3c, i.e. amino acids at positions 826 to 836, differ from those in the corresponding region of EAA3a as shown in FIG. 4B (SEQ ID NOS. 7–10). In comparison to EAA3a, the EAA3d receptor (SEQ ID NO:18) has a 56 amino acid deletion at its N-terminal end, i.e. the amino acids at positions 6 to 61 in EAA3a are deleted from EAA3d (FIG. 4C (SEQ ID NOS. 11–14).

Like other members of the human EAA3 receptor family, EAA3a is characterized by a pharmacological profile i.e. a ligand binding "signature", that points strongly to a kainate-type pharmacology, as distinct from other excitatory amino acid receptor types, such as NMDA and AMPA. In addition, and despite the understanding that kainate binding receptors require a multi- and perhaps heteromeric subunit structure to function in the pharmacological sense, it has been found that cells producing the unitary EAA3a receptor do, independently of association with other receptor subunits, provide a reliable indication of excitatory amino acid binding. Thus, in a key aspect of the present invention, the human EAA3a receptor is exploited for the purpose of screening candidate compounds for the ability to interact with the present receptors and/or the ability to compete with endogenous EAA receptor ligands and known synthetic analogues thereof, for EAA receptor interaction.

For use in assessing interaction between the receptor and a test ligand, it is desirable to construct by application of genetic engineering techniques a mammalian cell that produces a human EAA3 receptor in functional form as a heterologous product. The construction of such cell lines is achieved by introducing into a selected host cell a recombinant DNA construct in which DNA coding for a secretable form of the human EAA3 receptor, i.e., a form bearing either its native signal peptide or a functional, heterologous equivalent thereof, is associated with expression controlling elements that are functional in the selected host to drive expression of the receptor-encoding DNA, and thus elaborate the desired EAA3 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host.

It is most desirable to use a mammalian cell host to produce EAA3 receptors due to the mammalian origin of the present EAA3 receptors; however, other suitably engineered eukaryotic and prokaryotic hosts may also be employed to produce EAA3 receptors. Accordingly, bacterial hosts such as *E. coli* and *B. subtilis*, fungal hosts such as Aspergillus and yeast and insect cell hosts such as *Spodoptera frugiperda*, are examples of non-mammalian hosts that may also be used to produce EAA3 receptors of the present invention.

The particular cell type selected to serve as host for production of the human EAA3 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for EAA3 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells; human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be exploited to drive expression of the EAA3 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for a secretable form of the receptor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E.coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as steroid-inducible promoters and those regulated by heavy metals i.e. the metallothionein gene promoter.

For incorporation into the recombinant DNA expression vector, DNA coding for the desired EAA3 receptor, e.g. the EAA3a receptor or a kainate-binding variant thereof, can be obtained by applying selected techniques of gene isolation or gene synthesis. As described in more detail in the examples herein, the EAA3a receptor, and the EAA3b, EAA3c, and EAA3d variants thereof, are encoded within the genome of human brain tissue, and can therefore be obtained by careful application of conventional gene isolation and cloning techniques. This typically will entail extraction of total messenger RNA from a fresh source of human brain tissue, such as cerebellum or hippocampus tissue and preferably fetal brain tissue, followed by conversion of message to cDNA and formation of a library in for example a bacteria plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA3 receptors, it will be appreciated that automated techniques of gene synthesis and/or amplification can be performed to generate DNA coding therefor. Because of the length of EAA3 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA3 gene family. It will be appreciated that polynucleotides coding for the EAA3 receptors herein described can be generated by substituting synonymous codons for those represented in the naturally occurring polynucleotide sequences herein identified. In addition, polynucleotides coding for synthetic variants of the EAA3 receptors herein described can be generated which for example incorporate one or more single amino acid substitutions, deletions or additions. Since it will for the most part be desirable to retain the natural ligand and binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, microinjection, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR− cells into DHFR+ cells, and the tk gene of herpes simplex virus, which makes TK− cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and al washing must be done in a buffered medium, for example in phosphate-buffered saline, to avoid osmotic shock and rupture of the cells.

The EAA3 receptors of the present invention are per se functional in an electrophysiological context, and are therefore useful, in the established manner, in screening test ligands for their ability to modulate ion channel activity. The present invention thus further provides, as a ligand screening technique, a method of detecting interaction between a test ligand and a human CNS receptor, which comprises the steps of incubating the test ligand with a human EAA3 receptor-producing cell or with a membrane preparation derived therefrom, and then measuring ligand-induced electrical current across said cell or membrane.

As an alternative to using cells that express receptor-encoding DNA, ligand characterization may also be performed using cells, for example Xenopus oocytes, that yield functional membrane-bound receptor following introduction of messenger RNA coding for the EAA3 receptor. In this case, the EAA3 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested in either intact form or as a membrane preparation for the ability to bind a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell or placed on either side of a cell-derived membrane preparation using the "patch-clamp" technique.

The binding of a candidate ligand to a selected human EAA3 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that kainate-binding fragments, i.e., the portion of the EAA3 receptor responsible for binding a ligand molecule, resides on the outside of the cell, i.e., is extracellular. It is therefore desirable in the first instance to facilitate the characterization of the receptor-ligand interaction by providing such kainate binding fragments in quantity and in isolated form, i.e., free from the remainder of the receptor. To accomplish this, the full-length EAA3 receptor-encoding DNA may be modified by site-directed mutagenesis, to introduce a translational stop codon into the extracellular N-terminal region, immediately 5' of the first transmembrane domain (TM1), i.e., before the residue 533 codon as shown in FIGS. 1A–1J (SEQ ID NO:1). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce different versions of the extracellular regions, in order to map the ligand binding domain with precision. It will also be appreciated that the length of the fragment may be varied, i.e. to lengths less than the entire 533 amino acid extracellular N-terminal domain.

Alternatively, it may be desirable to produce an extracellular domain of the receptor which is not derived from the N-terminus of the mature protein, but rather from the C-terminus, for example domains immediately following the fourth transmembrane domain (TM4), i.e., residing between amino acid residues 811 and 875 inclusive as shown in FIGS. 1A–1J (SEQ ID NO:1). In this case, site-directed mutagenesis and/or PCR-based amplification techniques may readily be used to provide a defined fragment of the gene encoding the receptor domain of interest. Direct peptide synthesis may also be used to make the desired C-terminal fragment, or as noted above, desired N-terminal fragments. Such a DNA sequence may be use to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of an EAA3 receptor, for example in brain tissue, the present invention also provides, in another of its aspects, labelled antibody to a human EAA3 receptor. To raise such antibodies, there may be used as immunogen either the intact, soluble receptor or an immunogenic fragment thereof, produced in a microbial or mammalian cell host as described above or by standard peptide synthesis techniques. Regions of the EAA3a receptor particularly suitable for use as immunogenic fragments include those corresponding in sequence to an extracellular region of the receptor, or a portion of the extracellular region, such as peptides consisting of residues 1–532 or fragments thereof, including particularly residues 186–201 or 485–528, and peptides corresponding to the region between transmembrane domains TM-2 and TM-3, such as a peptide consisting of residues 595–604. Peptides consisting of the C-terminal domain (residues 811–875), or fragments thereof may also be used for the raising of antibodies. Substantially the same region of the human EAA3b, EAA3c and EAA3d receptor may also be used for production of antibodies against this receptor.

The raising of antibodies to the desired EAA3 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to myeloma cells. The fusion products, i.e. hybridomas, are then screened by culturing in a selection medium, and cells producing antibody are recovered for continuous growth, and antibody recovery. Recovered antibody can then be coupled covalently to a reporter molecule, i.e. a detectable label such as a radiolabel, enzyme label, luminescent label or the like, using linker technology established for this purpose, to form a specific probe for EAA3 receptors.

In detectably labelled form, e.g. radiolabelled form, DNA or RNA coding for the human EAA3 receptor, and selected regions thereof, may also be used, in accordance with another aspect of the present invention, as hybridization probes for example to identify sequence-related genes resident in the human or other mammalian genomes (or cDNA libraries) or to locate the EAA3-encoding DNA in a specimen, such as brain tissue. This can be done using either the intact coding region, or a fragment thereof having radiolabelled e.g. $^{32}$P, nucleotides incorporated therein. To identify the EAA3-encoding DNA in a specimen, it is desirable to use either the full length cDNA coding therefor, or a fragment which is unique thereto. With reference to FIGS. 1A–1J (SEQ ID NO:1) and the nucleotide numbering appearing thereon, such nucleotide fragments include those comprising at least about 17 nucleic acids, and otherwise corresponding in sequence to a region coding for the N-terminus or C-terminus of the receptor, or representing a 5'-untranslated or 3'-untranslated region thereof. Examples of suitable nucleotide fragments for this purpose include nucleotides 426–446 and nucleotides 1251–1271 of EAA3a. These sequences, among others, as well as the intact gene itself, may also be used of course to clone EAA3-related human genes, particularly cDNA equivalents thereof, by standard hybridization techniques.

Embodiments of the present invention are described in detail in the following non-limiting Examples.

EXAMPLE 1

Isolation of DNA Coding for the Human EAA3a Receptor cDNA coding for the human EAA3 receptor was identified by probing human fetal brain cDNA that was obtained as an EcoRI-based lambda phage library (lambda ZAP) from Stratagene Cloning Systems (La Jolla, Calif., U.S.A.). The cDNA library was screened using an oligonucleotide probe having the following specific sequence (SEQ ID NO:15):

5'-ATCGGCGGCATCTTCATTGTTCTGGCTG-
CAGGACTCGTGC-3'

The fetal brain cDNA library was screened under the following hybridization conditions; 6×SSC, 25% formamide, 5× Denhardt's solution, 10 mM Na$_2$HPO$_4$ buffer, 0.5% sodium pyrophosphate, 0.5% SDS, 100 μg/ml denatured salmon sperm DNA, 42° C. Filters were washed with 6×SSC containing 0.5% SDS at 25° C. for 5 minutes, followed by a 15 minute wash at 42° C. with 2×SSC containing 0.5% SDS. The final wash was with 1×SSC containing 0.5% SDS at 50° C. for 15 minutes. Filters were exposed to X-ray film (Kodak) overnight. Of 10$^6$ clones screened, only two cDNA inserts were identified; one of about 0.9 kb designated RKCSFG72, and another of about 2.7 kb designated RKCS5F81. For sequencing, the '72 and '81 phages were plaque purified, then excised as phagemids according to the supplier's specifications, to generate insert-carrying Bluescript-SK variants of the phagemid vectors. Sequencing of the '72 clone across its entire sequence revealed an open reading frame representing the C-terminal region but no putative termination codon. Sequencing across the '81 insert revealed a DNA sequence with about 80% identity with the '72 clone. The '81 clone displayed significant overlap to the '72 clone and included an additional 5' sequence.

Since no initiation and termination codons were apparent in the '72 sequence, the 5' and 3' regions of the '72 clone was sought. For this purpose, a 2.0 kb EcoRI fragment representing the '81 clone and a 0.9 kb EcoRI fragment representing the '72 clone were isolated, $^{32}$P-labelled, and then used to re-screen the same fetal brain cDNA library under the following hybridization conditions: 6×SSC, 25% formamide, 5× Denhardt's solution, 0.5% SDS, 100 μg/ml denatured salmon sperm DNA, 30° C. Filters were washed twice with 2×SSC containing 0.5% SDS at 25° C. for 5 minutes, followed by a 15 minute final wash at 42° C. with 2×SSC containing 0.5% SDS. Filters were exposed to X-ray film (Kodak) overnight. Of 10$^6$ clones screened, only two cDNA were identified, one of about 1.5 kb designated RKCS221, and the another of about 1.8 kb designated RKC41. Sequencing the entire '221 insert revealed more of the 5' sequence of the '72 clone as well as a termination codon and about 250 bases of the 3' non-coding region. Sequencing the entire '41 insert revealed more of the 5' sequence but still did not reveal an initiation codon.

Thus, the same fetal brain cDNA library was screened using an oligonucleotide probe (based on the '41 sequence) capable of annealing to the 5' region of the '41 sequence. The specific sequence (SEQ ID NO:16) of the 32P-labelled probe is provided below:

5'-CCATCATTGAGAAGTGGTCC-3'

This probe was $^{32}$P-labelled and then used to re-screen the same fetal brain cDNA library under the following hybridization conditions: 6×SSC, 50% formamide, 5× Denhardt's solution, 0.5% SDS, 100 μg/ml denatured salmon sperm DNA, 30° C. Filters were washed twice with 2×SSC containing 0.5% SDS at 25° C. for 5 minutes, followed by a 15 minute final wash at 42° C. with 2×SSC containing 0.5% SDS. Filters were exposed to X-ray film (Kodak) overnight. Of 10$^6$ clones screened, a single cDNA insert was identified of about 1.7 kb designated RKS71. The '71 insert, when sequenced, revealed the initiation codon together with about 417 bases of 5' non-coding region and a significant overlap with the '41 insert.

To provide the entire coding region of the receptor, the strategy depicted in FIG. 2 was then applied to generate the 6.3 kb phagemid pBS/humEAA3a which carries the intact EAA3a receptor-encoding DNA as a 3.3 kb NotI/HindIII insert in a 3.0 kb pBluescript phagemid background. Phagemid pBS/humEAA3a was deposited under the terms of the Budapest Treaty with the American Type Culture Collection in Rockville, Md. USA on Nov. 12, 1992, and has been assigned accession number ATCC 75350.

EXAMPLE 2

Construction of Genetically Engineered Cells Producing the Human EAA3a Receptor

Figure 3:
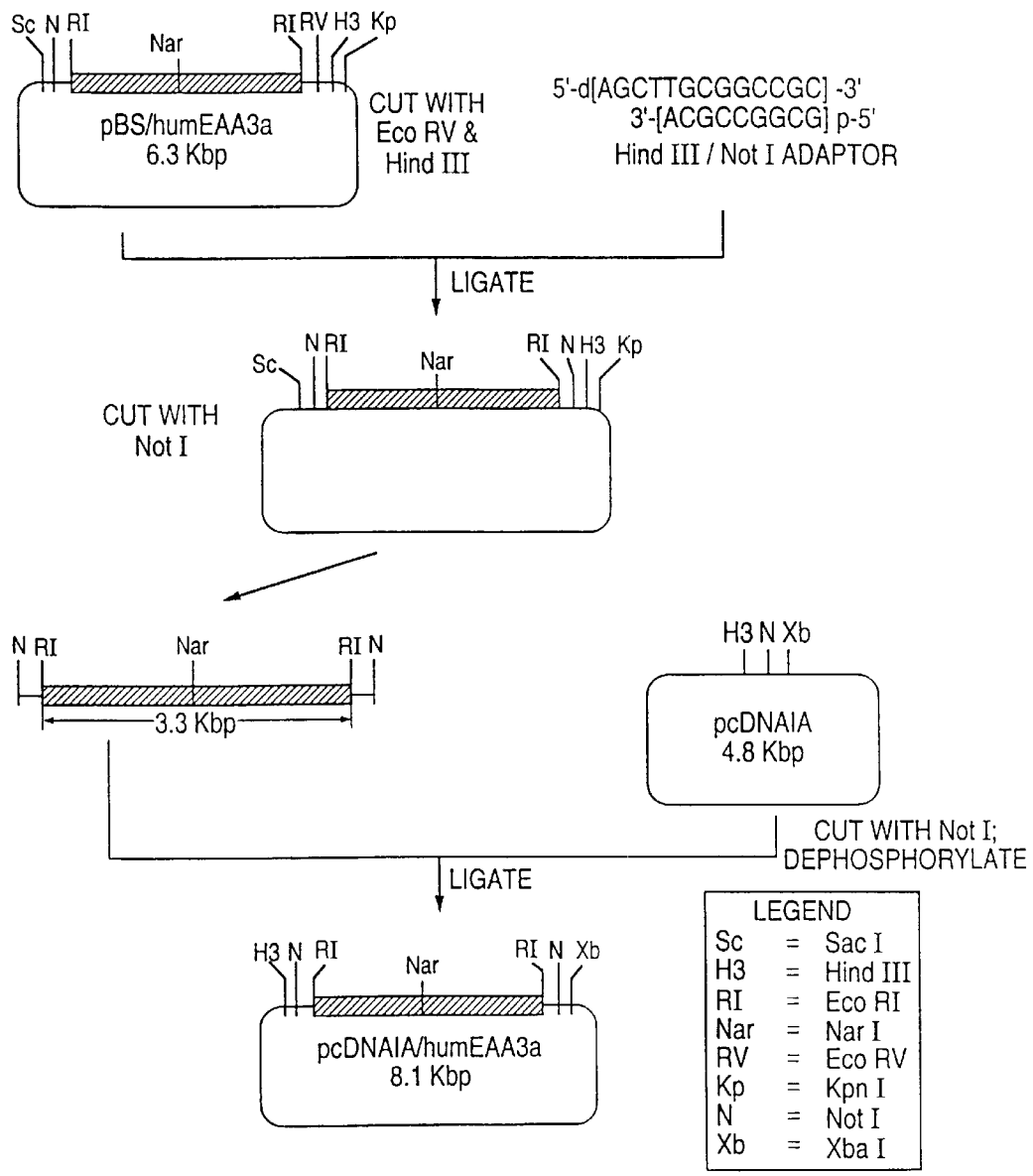
FIG. 3 illustrates with plasmid maps the strategy used to construct expression vectors harbouring the DNA sequence illustrated in FIGS. 1A–1J provide (SEQ ID NO:1)

For transient expression in mammalian cells, cDNA encoding the EAA3a receptor was incorporated into the mammalian expression vector pcDNAI/Amp (pcDNAIA), which is available commercially from Invitrogen Corporation (San Diego, Calif., USA: catalogue number V490-20), as depicted in FIG. 3. pcDNAIA is a multifunctional 4.8 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, M13 origin to rescue single strand DNA for sequencing and mutagenesis, Sp6 and T7 RNA promoters for the production of sense and anti-sense RNA transcripts and a Col El-like high copy plasmid origin. A polylinker is located appropriately downstream of the CMV promoter and 3' of the T7 promoter.

Briefly, the EAA3a-encoding cDNA insert was released from pBS/humEAA3a as a 3.3 kb NotI/NotI fragment subsequent to insertion of a HindIII/NotI adaptor at the 3' end of the insert. The 3.3 kb fragment was then incorporated at the NotI site in the pcDNAIA vector to form the expression vector pcDNAIA/humEAA3a.

For transient expression of the EAA3-encoding DNA, monkey-derived, fibroblast-like cells of the COS-1 lineage (available from the American Type Culture Collection, Rockville, Md. as ATCC CRL 1650) were transfected with approximately 8 ug DNA (as pcDNAIA/humEAA3a) per $10^6$ COS cells, by DEAE-mediated DNA transfection and treated with chloroquine according to conventional procedures. Briefly, COS-1 cells were plated at a density of $5 \times 10^6$ cells/dish and then grown for 24 hours in FBS-supplemented DMEM/F12 medium. Medium was then removed and cells were washed with PBS and then with medium. There was then applied on the cells 10 ml of a transfection solution containing DEAE dextran (0.4 mg/ml), 100 $\mu$M chloroquine, 10% NuSerum, DNA (0.4 mg/ml) in DMEM/F12 medium. After incubation for 3 hours at 37° C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, the cells were washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also be prepared using two different cell types as host: CHO K1 and CHO Pro5. To construct these cell lines, cDNA coding for human EAA3a is incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented $\alpha$MEM medium. After growth for 24 hours, fresh medium is added to the plates and three hours later, the cells are transfected using the conventional calcium phosphate-DNA co-precipitation procedure. Briefly, 3 $\mu$g of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilled water using a hand homogenizer and centrifuged for 20 minutes at 50,000 g. The supernatant was discarded and the membrane pellet stored frozen at $-70°$ C.

COS cell membrane pellets were suspended in ice cold 50 mM Tris-HCl (pH 7.55, 5° C.) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to 25–100 ug as judged by protein determination and selected radiolabelled ligand. In particular, for kainate binding assays, incubation mixtures consisted of 25–100 $\mu$g tissue protein and [vinylidene-3H] kainic acid (58 Ci/mmole, 80 nM final) in the cold incubation buffer, 1 ml final volume. Non-specific binding was in the presence of 1 mM L-glutamate. Samples were incubated on ice for 60 minutes, and bound and free ligated were then separated by rapid filtration using a PHD cell harvester and GF/B filters pre-soaked in ice-cold 0.3% polyethyleneimine. Filters were washed twice in 4 ml of the cold incubation buffer, then placed in scintillation vials with 5 ml of Beckman Ready-Protein Plus scintillation cocktail for counting.

For AMPA-binding assays, incubation mixtures consisted of 25–100 ug tissue protein and D,L-$\alpha$-[5-methyl-3H] amino-3-hydroxy-5-methylisoxazole-4-propionic acid (3H-AMPA, 27.6 Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

Assays performed in this manner, using membrane preparations derived from the EAA3a-producing COS cells, revealed specific [3H]-kainate binding of 167 fmol/mg protein at 80 nM, labelled ligand (FIG. 4). Mock transfected cells exhibited no specific binding of any of the ligands tested. These results demonstrate clearly that the human EAA3a receptor is binding kainate specifically. This activity, coupled with the fact that there is little or no demonstrable binding of either AMPA or NMDA clearly assigns the EAA3a receptor to be one of the kainate type of EAA receptor. Furthermore, this binding profile indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displaying other ligands from the receptor. The isolation of the EAA3a receptor gene in a pure form, capable of being expressed as a single, homogenous receptor species, therefore frees the ligand binding assay from the lack of precision introduced when complex, heterogeneous receptor preparations from human and non-human brains are used to attempt such characterizations.

We claim:

1. A human EAA3 receptor in a form essentially free from other proteins of human origin, selected from the group consisting of:

a human EAA3a protein having the sequence of amino acids 1–875 of SEQ ID NO:2; and a human EAA3b protein having the sequence of amino acids 1–875 of SEQ ID NO:2 in which the amino acid residue at position 639 has been replaced by asparagine.

2. A human EAA3 receptor as defined in claim 1 which is the human EAA3a protein.

3. A human EAA3 receptor as defined in claim 1, which is the human EAA3b protein.

4. A fragment of a human EAA3 receptor, wherein the EAA3 receptor is selected from the group consisting of:
a human EAA3a protein having the sequence of amino acids 1–875 of SEQ ID NO:2; and
a human EAA3b protein having the sequence of amino acids 1–875 of SEQ ID NO:2 in which the amino acid residue at position 639 has been replaced by asparagine,
wherein said fragment comprises any one of the extracellular N-terminus that precedes the TM-1, the extracellular C-terminal region that follows TM-4, and the region between TM-3 and TM-4.

5. A fragment according to claim 4, which is a fragment of the human EAA3a protein.

6. A fragment as claimed in claim 4, wherein said fragment comprises the extracellular N-terminus.

7. A fragment as claimed in claim 4, wherein said fragment has a sequence that comprises a region between transmembrane domains TM-3 and TM-4.

8. A fragment as claimed in claim 4, wherein said fragment comprises the extracellular C-terminal region that follows the fourth transmembrane domain.

9. A fragment according to claim 4, which is a fragment of the human EAA3b protein.

10. An immunogenic fragment of a human EAA3 receptor, wherein the EAA3 receptor is selected from the group consisting of:
a human EAA3a protein having the sequence of amino acids 1–875 of SEQ ID NO:2; and
a human EAA3b protein having the sequence of amino acids 1–875 of SEQ ID NO:2 in which the amino acid residue at position 639 has been replaced by asparagine,
wherein said fragment comprises the N-terminal or C-terminal extracellular region of said protein.

11. An immunogenic fragment of a human EAA3 receptor according to claim 10, which is an immunogenic fragment of the human EAA3a protein.

12. A variant of a human EAA3 receptor, in a form essentially free from other proteins of human origin, which is a variant having a sequence of amino acids 1–875 of SEQ ID NO:2 with the exception that there are from 1–32 conservative amino acid substitution.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 3385 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 418..3132

(ix) FEATURE:
      (A) NAME/KEY: mat_peptide
      (B) LOCATION: 508..3132

(ix) FEATURE:
      (A) NAME/KEY: sig_peptide
      (B) LOCATION: 418..507

(xi) SEQUENCE DESCRIPTION: SEQ ID NO:1:

```
GAATTCCGTC TTCTTTCCCC CTTTTCCCTC CTCTGTCTGT GCCTATCCCC CGACTTTTGC     60

ATCTGACCAA AGGACGAATG AGGGAGACGT TCCTGCAGAT CGGGGCAGCA ACTTTCCTCA    120

GCTGGTCTCT GGGCTCCGGA GCCAGAGAGC GCTGATCCTC CGCGTCTGCG GCCCATGAAG    180

AGAGAGAGAG CCGTGATGGG CTAGCGACAG CACTGAGGAG CCCCGAGAGA GCTCAGCCTT    240

GCCAGCCAGC TCCGCGGTCC CACGCGGGTT CCCTCGAGCT CGCTCCGTGG GGAGCGCGCA    300

GCGTGCTTGG AACGGAGCA TCCAGAGAGG ATGAGGCGGG GACCCGGCCC AAGTTGGGTG     360

CATCTCTCGG GCGTCCGGCA GCGGCTGTAT CTCGGCATGA ATTAAGAAGC TAGGAAG       417

ATG GAG CAC GGC ACA CTC CTC GCC CAG CCC GGG CTC TGG ACC AGG GAC      465
Met Glu His Gly Thr Leu Leu Ala Gln Pro Gly Leu Trp Thr Arg Asp
-30                 -25                 -20                 -15

ACC AGC TGG GCA CTC CTC TAT TTC CTC TGC TAT ATC CTC CCT CAG ACC      513
Thr Ser Trp Ala Leu Leu Tyr Phe Leu Cys Tyr Ile Leu Pro Gln Thr
            -10                  -5                   1

GCC CCG CAA GTA CTC AGG ATC GGA GGG ATT TTT GAA ACA GTG GAA AAT      561
Ala Pro Gln Val Leu Arg Ile Gly Gly Ile Phe Glu Thr Val Glu Asn
                5                  10                  15

GAG CCT GTT AAT GTT GAA GAA TTA GCT TTC AAG TTT GCA GTC ACC AGC      609
Glu Pro Val Asn Val Glu Glu Leu Ala Phe Lys Phe Ala Val Thr Ser
        20                  25                  30

ATT AAC AGA AAC CGA ACC CTG ATG CCT AAC ACC ACA TTA ACC TAT GAC      657
Ile Asn Arg Asn Arg Thr Leu Met Pro Asn Thr Thr Leu Thr Tyr Asp
 35                  40                  45                  50

ATC CAG AGA ATT AAC CTT TTT GAT AGT TTT GAA GCC TCG CGG AGA GCA      705
Ile Gln Arg Ile Asn Leu Phe Asp Ser Phe Glu Ala Ser Arg Arg Ala
                    55                  60                  65

TGT GAC CAG CTG GCT CTT GGT GTG GCT GCT CTC TTT GGC CCT TCC CAT      753
Cys Asp Gln Leu Ala Leu Gly Val Ala Ala Leu Phe Gly Pro Ser His
            70                  75                  80

AGC TCC TCC GTC AGT GCT GTG CAG TCT ATT TGC AAT GCT CTC GAA GTT      801
Ser Ser Ser Val Ser Ala Val Gln Ser Ile Cys Asn Ala Leu Glu Val
        85                  90                  95

CCA CAC ATA CAG ACC CGC TGG AAA CAC CCC TCG GTG GAC AAC AAA GAT      849
Pro His Ile Gln Thr Arg Trp Lys His Pro Ser Val Asp Asn Lys Asp
```

```
                 100                    105                        110
TTG TTT TAC ATC AAC CTT TAC CCA GAT TAT GCA GCT ATC AGC AGG GCG        897
Leu Phe Tyr Ile Asn Leu Tyr Pro Asp Tyr Ala Ala Ile Ser Arg Ala
115             120                 125                 130

ATC CTG GAT CTG GTC CTC TAT TAC AAC TGG AAA ACA GTG ACA GTG GTG        945
Ile Leu Asp Leu Val Leu Tyr Tyr Asn Trp Lys Thr Val Thr Val Val
                135                 140                 145

TAT GAA GAC AGC ACA GGT CTA ATT CGT CTA CAA GAG CTC ATC AAA GCT        993
Tyr Glu Asp Ser Thr Gly Leu Ile Arg Leu Gln Glu Leu Ile Lys Ala
            150                 155                 160

CCC TCC AGA TAT AAT ATT AAA ATC AAA ATC CGC CAG CTG CCC TCT GGG       1041
Pro Ser Arg Tyr Asn Ile Lys Ile Lys Ile Arg Gln Leu Pro Ser Gly
        165                 170                 175

AAT AAA GAT GCC AAG CCT TTA CTC AAG GAG ATG AAG AAA GGC AAG GAG       1089
Asn Lys Asp Ala Lys Pro Leu Leu Lys Glu Met Lys Lys Gly Lys Glu
    180                 185                 190

TTC TAT GTG ATA TTT GAT TGT TCA CAT GAA ACA GCC GCT GAA ATC CTT       1137
Phe Tyr Val Ile Phe Asp Cys Ser His Glu Thr Ala Ala Glu Ile Leu
195                 200                 205                 210

AAG CAG ATT CTG TTC ATG GGC ATG ATG ACC GAA TAC TAT CAC TAC TTT       1185
Lys Gln Ile Leu Phe Met Gly Met Met Thr Glu Tyr Tyr His Tyr Phe
                215                 220                 225

TTC ACA ACC CTG GAC TTA TTT GCT TTG GAT CTG GAA CTC TAT AGG TAC       1233
Phe Thr Thr Leu Asp Leu Phe Ala Leu Asp Leu Glu Leu Tyr Arg Tyr
            230                 235                 240

AGT GGC GTA AAC ATG ACC GGG TTT GGG CTG CTT AAC ATT GAC AAC CCT       1281
Ser Gly Val Asn Met Thr Gly Phe Gly Leu Leu Asn Ile Asp Asn Pro
        245                 250                 255

CAC GTG TCA TCC ATC ATT GAG AAG TGG TCC ATG GAG AGA CTG CAG GCC       1329
His Val Ser Ser Ile Ile Glu Lys Trp Ser Met Glu Arg Leu Gln Ala
    260                 265                 270

CCA CCC AGG CCC GAG ACT GGC CTT TTG GAT GGC ATG ATG ACA ACT GAA       1377
Pro Pro Arg Pro Glu Thr Gly Leu Leu Asp Gly Met Met Thr Thr Glu
275                 280                 285                 290

GCG GCT CTG ATG TAC GAT GCT GTG TAC ATG GTG GCC ATT GCC TCG CAC       1425
Ala Ala Leu Met Tyr Asp Ala Val Tyr Met Val Ala Ile Ala Ser His
                295                 300                 305

CGG GCA TCC CAG CTG ACC GTC AGC TCC CTG CAG TGC CAT AGA CAT AAG       1473
Arg Ala Ser Gln Leu Thr Val Ser Ser Leu Gln Cys His Arg His Lys
            310                 315                 320

CCA TGG CGC CTC GGA CCC AGA TTT ATG AAC CTG ATC AAA GAG GCC CGG       1521
Pro Trp Arg Leu Gly Pro Arg Phe Met Asn Leu Ile Lys Glu Ala Arg
        325                 330                 335

TGG GAT GGC TTG ACT GGG CAT ATC ACC TTT AAT AAA ACC AAT GGC TTG       1569
Trp Asp Gly Leu Thr Gly His Ile Thr Phe Asn Lys Thr Asn Gly Leu
    340                 345                 350

AGG AAG GAT TTT GAT CTG GAC ATT ATT AGT CTC AAA GAG GAA GGA ACT       1617
Arg Lys Asp Phe Asp Leu Asp Ile Ile Ser Leu Lys Glu Glu Gly Thr
355                 360                 365                 370

GAA AAG ATT GGG ATT TGG AAT TCC AAC AGT GGG CTT AAC ATG ACG GAC       1665
Glu Lys Ile Gly Ile Trp Asn Ser Asn Ser Gly Leu Asn Met Thr Asp
                375                 380                 385

AGC AAC AAA GAC AAG TCC AGC AAT ATC ACT GAT TCA TTG GCC AAC AGA       1713
Ser Asn Lys Asp Lys Ser Ser Asn Ile Thr Asp Ser Leu Ala Asn Arg
            390                 395                 400

ACA CTC ATT GTC ACC ACC ATT CTG GAA GAA CCC TAT GTT ATG TAC AGG       1761
Thr Leu Ile Val Thr Thr Ile Leu Glu Glu Pro Tyr Val Met Tyr Arg
        405                 410                 415

AAA TCT GAT AAG CCT CTA TAT GGA AAT GAC AGA TTT GAA GGA TAT TGC       1809
Lys Ser Asp Lys Pro Leu Tyr Gly Asn Asp Arg Phe Glu Gly Tyr Cys
```

-continued

```
              420                 425                 430
CTA GAC CTG TTG AAA GAA TTG TCA AAC ATC CTG GGT TTC ATT TAT GAT    1857
Leu Asp Leu Leu Lys Glu Leu Ser Asn Ile Leu Gly Phe Ile Tyr Asp
435             440                 445                 450

GTT AAA CTA GTT CCC GAT GGC AAA TAT GGG GCC CAG AAT GAC AAA GGG    1905
Val Lys Leu Val Pro Asp Gly Lys Tyr Gly Ala Gln Asn Asp Lys Gly
                        455                 460                 465

GAG TGG AAC GGG ATG GTT AAA GAA CTC ATA GAT CAC AGG GCT GAC CTG    1953
Glu Trp Asn Gly Met Val Lys Glu Leu Ile Asp His Arg Ala Asp Leu
                470                 475                 480

GCA GTG GCT CCT CTT ACC ATC ACC TAC GTG CGG GAG AAA GTC ATT GAC    2001
Ala Val Ala Pro Leu Thr Ile Thr Tyr Val Arg Glu Lys Val Ile Asp
            485                 490                 495

TTC TCC AAA CCC TTC ATG ACC CTA GGC ATC AGC ATT CTC TAC CGG AAG    2049
Phe Ser Lys Pro Phe Met Thr Leu Gly Ile Ser Ile Leu Tyr Arg Lys
500                 505                 510

CCC AAT GGT ACC AAT CCA GGC GTT TTC TCC TTC CTC AAC CCC CTG TCT    2097
Pro Asn Gly Thr Asn Pro Gly Val Phe Ser Phe Leu Asn Pro Leu Ser
515                 520                 525                 530

CCA GAT ATT TGG ATG TAT GTG CTC TTA GCC TGC TTG GGA GTC AGC TGT    2145
Pro Asp Ile Trp Met Tyr Val Leu Leu Ala Cys Leu Gly Val Ser Cys
                535                 540                 545

GTA CTC TTT GTG ATT GCA AGG TTT ACA CCC TAC GAG TGG TAT AAC CCC    2193
Val Leu Phe Val Ile Ala Arg Phe Thr Pro Tyr Glu Trp Tyr Asn Pro
            550                 555                 560

CAC CCA TGC AAC CCT GAC TCA GAC GTG GTG GAA AAC AAT TTT ACT TTA    2241
His Pro Cys Asn Pro Asp Ser Asp Val Val Glu Asn Asn Phe Thr Leu
        565                 570                 575

CTA AAT AGT TTC TGG TTT GGA GTT GGA GCT CTC ATG CAG CAA GGA TCA    2289
Leu Asn Ser Phe Trp Phe Gly Val Gly Ala Leu Met Gln Gln Gly Ser
580                 585                 590

GAG CTG ATG CCC AAA GCT CTA TCG ACC AGA ATA GTT GGA GGG ATA TGG    2337
Glu Leu Met Pro Lys Ala Leu Ser Thr Arg Ile Val Gly Gly Ile Trp
595                 600                 605                 610

TGG TTT TTC ACC CTA ATC ATC ATT TCA TCC TAC ACG GCC AAT CTG GCT    2385
Trp Phe Phe Thr Leu Ile Ile Ile Ser Ser Tyr Thr Ala Asn Leu Ala
                615                 620                 625

GCC TTC TTG ACA GTA GAG AGA ATG GAA TCC CCC ATA GAT TCG GCA GAT    2433
Ala Phe Leu Thr Val Glu Arg Met Glu Ser Pro Ile Asp Ser Ala Asp
            630                 635                 640

GAT CTG GCA AAG CAA ACC AAG ATA GAA TAT GGG GCG GTT AGA GAT GGA    2481
Asp Leu Ala Lys Gln Thr Lys Ile Glu Tyr Gly Ala Val Arg Asp Gly
        645                 650                 655

TCA ACA ATG ACC TTC TTC AAG AAA TCA AAA ATC TCC ACC TAT GAG AAG    2529
Ser Thr Met Thr Phe Phe Lys Lys Ser Lys Ile Ser Thr Tyr Glu Lys
660                 665                 670

ATG TGG GCT TTC ATG AGC AGC AGG CAG CAG ACC GCC CTG GTA AGA AAC    2577
Met Trp Ala Phe Met Ser Ser Arg Gln Gln Thr Ala Leu Val Arg Asn
675                 680                 685                 690

AGT GAT GAG GGG ATC CAG AGA GTG CTC ACC ACA GAC TAC GCG CTG CTG    2625
Ser Asp Glu Gly Ile Gln Arg Val Leu Thr Thr Asp Tyr Ala Leu Leu
                695                 700                 705

ATG GAG TCC ACC AGC ATT GAG TAT GTG ACG CAG AGA AAC TGC AAC CTC    2673
Met Glu Ser Thr Ser Ile Glu Tyr Val Thr Gln Arg Asn Cys Asn Leu
            710                 715                 720

ACT CAG ATC GGG GGC CTC ATT GAC TCC AAA GGT TAC GGA GTG GGA ACA    2721
Thr Gln Ile Gly Gly Leu Ile Asp Ser Lys Gly Tyr Gly Val Gly Thr
        725                 730                 735

CCT ATT GGT TCT CCT TAC CGG GAT AAA ATT ACT ATT GCT ATT CTT CAA    2769
Pro Ile Gly Ser Pro Tyr Arg Asp Lys Ile Thr Ile Ala Ile Leu Gln
```

| | | | | | | | | | | | | | | |
|---|---|---|---|---|---|---|---|---|---|---|---|---|---|---|
| | | 740 | | | | 745 | | | | | 750 | | | |
| CTC | CAA | GAA | GAA | GGG | AAG | CTG | CAT | ATG | ATG | AAA | GAG | AAG | TGG TGG CGT | 2817 |
| Leu | Gln | Glu | Glu | Gly | Lys | Leu | His | Met | Met | Lys | Glu | Lys | Trp Trp Arg | |
| 755 | | | | | 760 | | | | | 765 | | | 770 | |
| GGG | AAT | GGC | TGC | CCC | GAG | GAA | GAC | AAC | AAA | GAA | GCC | AGT | GCC CTG GGA | 2865 |
| Gly | Asn | Gly | Cys | Pro | Glu | Glu | Asp | Asn | Lys | Glu | Ala | Ser | Ala Leu Gly | |
| | | | | 775 | | | | | 780 | | | | 785 | |
| GTG | GAA | AAT | ATT | GGA | GGC | ATC | TTC | ATT | GTT | CTG | GCT | GCC | GGA CTG GTC | 2913 |
| Val | Glu | Asn | Ile | Gly | Gly | Ile | Phe | Ile | Val | Leu | Ala | Ala | Gly Leu Val | |
| | | | 790 | | | | | 795 | | | | | 800 | |
| CTT | TCT | GTA | TTT | GTA | GCT | ATT | GGA | GAA | TTC | ATA | TAC | AAA | TCA CGG AAG | 2961 |
| Leu | Ser | Val | Phe | Val | Ala | Ile | Gly | Glu | Phe | Ile | Tyr | Lys | Ser Arg Lys | |
| | | 805 | | | | | 810 | | | | | 815 | | |
| AAT | AAT | GAT | ATT | GAA | CAG | TGT | CTC | TCT | TTC | AAC | GCT | ATC | ATG GAA GAA | 3009 |
| Asn | Asn | Asp | Ile | Glu | Gln | Cys | Leu | Ser | Phe | Asn | Ala | Ile | Met Glu Glu | |
| | | 820 | | | | | 825 | | | | | 830 | | |
| CTG | GGA | ATC | TCA | CTG | AAG | AAT | CAG | AAA | AAA | ATA | AAG | AAA | AAG TCA AGA | 3057 |
| Leu | Gly | Ile | Ser | Leu | Lys | Asn | Gln | Lys | Lys | Ile | Lys | Lys | Lys Ser Arg | |
| 835 | | | | | 840 | | | | | 845 | | | 850 | |
| ACT | AAG | GGG | AAA | TCT | TCC | TTC | ACA | AGT | ATC | CTT | ACT | TGT | CAT CAG AGA | 3105 |
| Thr | Lys | Gly | Lys | Ser | Ser | Phe | Thr | Ser | Ile | Leu | Thr | Cys | His Gln Arg | |
| | | | | 855 | | | | | 860 | | | | 865 | |
| CGA | ACT | CAG | AGA | AAA | GAG | ACT | GTG | GCG | TGATCCAAGG AAACGCCTGT | | | | | 3152 |
| Arg | Thr | Gln | Arg | Lys | Glu | Thr | Val | Ala | | | | | | |
| | | | 870 | | | | 875 | | | | | | | |

AGGAAGAAAA AGGATGCATT CCCTACAGAT TTTTGGAGAA AGGATTTCTG AGGAGTTGTG    3212

TGATGTGTTT CCATATATCT ATATCCATAA CTCTGATTAT GAATACAGAT ATAAGAAATA    3272

CAAAAGTTTA AAAAGCTCAC ATAGATATGA CTTGGGAAGT GACACCAGTT CTTTTAAAAT    3332

AAATTTGTAT GCACAAAAAA AAAAAAAAAA AAAAAAAAA AAAAAAGGAA TTC            3385

(2) INFORMATION FOR SEQ ID NO:2:

(i) SEQUENCE CHARACTERISTICS:
        (A) LENGTH: 905 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | |
|---|---|---|---|---|---|---|---|---|---|---|---|---|
| Met | Glu | His | Gly | Thr | Leu | Leu | Ala | Gln | Pro | Gly | Leu | Trp Thr Arg Asp |
| -30 | | | | | -25 | | | | | -20 | | -15 |
| Thr | Ser | Trp | Ala | Leu | Leu | Tyr | Phe | Leu | Cys | Tyr | Ile | Leu Pro Gln Thr |
| | | | | -10 | | | | | -5 | | | 1 |
| Ala | Pro | Gln | Val | Leu | Arg | Ile | Gly | Gly | Ile | Phe | Glu | Thr Val Glu Asn |
| | 5 | | | | | 10 | | | | | 15 | |
| Glu | Pro | Val | Asn | Val | Glu | Glu | Leu | Ala | Phe | Lys | Phe | Ala Val Thr Ser |
| | 20 | | | | | 25 | | | | | 30 | |
| Ile | Asn | Arg | Asn | Arg | Thr | Leu | Met | Pro | Asn | Thr | Thr | Leu Thr Tyr Asp |
| 35 | | | | | 40 | | | | | 45 | | 50 |
| Ile | Gln | Arg | Ile | Asn | Leu | Phe | Asp | Ser | Phe | Glu | Ala | Ser Arg Arg Ala |
| | | | | 55 | | | | | 60 | | | 65 |
| Cys | Asp | Gln | Leu | Ala | Leu | Gly | Val | Ala | Ala | Leu | Phe | Gly Pro Ser His |
| | | | 70 | | | | | 75 | | | | 80 |
| Ser | Ser | Ser | Val | Ser | Ala | Val | Gln | Ser | Ile | Cys | Asn | Ala Leu Glu Val |
| | | | | 85 | | | | | 90 | | | 95 |
| Pro | His | Ile | Gln | Thr | Arg | Trp | Lys | His | Pro | Ser | Val | Asp Asn Lys Asp |
| | 100 | | | | | 105 | | | | | 110 | |

-continued

Leu Phe Tyr Ile Asn Leu Tyr Pro Asp Tyr Ala Ala Ile Ser Arg Ala
115                 120                 125                 130

Ile Leu Asp Leu Val Leu Tyr Tyr Asn Trp Lys Thr Val Thr Val Val
            135                 140                 145

Tyr Glu Asp Ser Thr Gly Leu Ile Arg Leu Gln Glu Leu Ile Lys Ala
                150                 155                 160

Pro Ser Arg Tyr Asn Ile Lys Ile Lys Ile Arg Gln Leu Pro Ser Gly
            165                 170                 175

Asn Lys Asp Ala Lys Pro Leu Leu Lys Glu Met Lys Lys Gly Lys Glu
180                 185                 190

Phe Tyr Val Ile Phe Asp Cys Ser His Glu Thr Ala Ala Glu Ile Leu
195                 200                 205                 210

Lys Gln Ile Leu Phe Met Gly Met Met Thr Glu Tyr Tyr His Tyr Phe
                215                 220                 225

Phe Thr Thr Leu Asp Leu Phe Ala Leu Asp Leu Glu Leu Tyr Arg Tyr
            230                 235                 240

Ser Gly Val Asn Met Thr Gly Phe Gly Leu Leu Asn Ile Asp Asn Pro
            245                 250                 255

His Val Ser Ser Ile Ile Glu Lys Trp Ser Met Glu Arg Leu Gln Ala
260                 265                 270

Pro Pro Arg Pro Glu Thr Gly Leu Leu Asp Gly Met Met Thr Thr Glu
275                 280                 285                 290

Ala Ala Leu Met Tyr Asp Ala Val Tyr Met Val Ala Ile Ala Ser His
                295                 300                 305

Arg Ala Ser Gln Leu Thr Val Ser Ser Leu Gln Cys His Arg His Lys
                310                 315                 320

Pro Trp Arg Leu Gly Pro Arg Phe Met Asn Leu Ile Lys Glu Ala Arg
            325                 330                 335

Trp Asp Gly Leu Thr Gly His Ile Thr Phe Asn Lys Thr Asn Gly Leu
            340                 345                 350

Arg Lys Asp Phe Asp Leu Asp Ile Ile Ser Leu Lys Glu Glu Gly Thr
355                 360                 365                 370

Glu Lys Ile Gly Ile Trp Asn Ser Asn Ser Gly Leu Asn Met Thr Asp
            375                 380                 385

Ser Asn Lys Asp Lys Ser Ser Asn Ile Thr Asp Ser Leu Ala Asn Arg
                390                 395                 400

Thr Leu Ile Val Thr Thr Ile Leu Glu Glu Pro Tyr Val Met Tyr Arg
            405                 410                 415

Lys Ser Asp Lys Pro Leu Tyr Gly Asn Asp Arg Phe Glu Gly Tyr Cys
420                 425                 430

Leu Asp Leu Leu Lys Glu Leu Ser Asn Ile Leu Gly Phe Ile Tyr Asp
435                 440                 445                 450

Val Lys Leu Val Pro Asp Gly Lys Tyr Gly Ala Gln Asn Asp Lys Gly
                455                 460                 465

Glu Trp Asn Gly Met Val Lys Glu Leu Ile Asp His Arg Ala Asp Leu
            470                 475                 480

Ala Val Ala Pro Leu Thr Ile Thr Tyr Val Arg Glu Lys Val Ile Asp
            485                 490                 495

Phe Ser Lys Pro Phe Met Thr Leu Gly Ile Ser Ile Leu Tyr Arg Lys
            500                 505                 510

Pro Asn Gly Thr Asn Pro Gly Val Phe Ser Phe Leu Asn Pro Leu Ser
515                 520                 525                 530

Pro Asp Ile Trp Met Tyr Val Leu Leu Ala Cys Leu Gly Val Ser Cys

-continued

```
                535                 540                 545
Val Leu Phe Val Ile Ala Arg Phe Thr Pro Tyr Glu Trp Tyr Asn Pro
            550                 555                 560
His Pro Cys Asn Pro Asp Ser Asp Val Val Glu Asn Asn Phe Thr Leu
            565                 570                 575
Leu Asn Ser Phe Trp Phe Gly Val Gly Ala Leu Met Gln Gln Gly Ser
            580                 585                 590
Glu Leu Met Pro Lys Ala Leu Ser Thr Arg Ile Val Gly Gly Ile Trp
595                 600                 605                 610
Trp Phe Phe Thr Leu Ile Ile Ile Ser Ser Tyr Thr Ala Asn Leu Ala
                615                 620                 625
Ala Phe Leu Thr Val Glu Arg Met Glu Ser Pro Ile Asp Ser Ala Asp
            630                 635                 640
Asp Leu Ala Lys Gln Thr Lys Ile Glu Tyr Gly Ala Val Arg Asp Gly
            645                 650                 655
Ser Thr Met Thr Phe Phe Lys Lys Ser Lys Ile Ser Thr Tyr Glu Lys
            660                 665                 670
Met Trp Ala Phe Met Ser Ser Arg Gln Gln Thr Ala Leu Val Arg Asn
675                 680                 685                 690
Ser Asp Glu Gly Ile Gln Arg Val Leu Thr Thr Asp Tyr Ala Leu Leu
                695                 700                 705
Met Glu Ser Thr Ser Ile Glu Tyr Val Thr Gln Arg Asn Cys Asn Leu
            710                 715                 720
Thr Gln Ile Gly Gly Leu Ile Asp Ser Lys Gly Tyr Gly Val Gly Thr
            725                 730                 735
Pro Ile Gly Ser Pro Tyr Arg Asp Lys Ile Thr Ile Ala Ile Leu Gln
            740                 745                 750
Leu Gln Glu Glu Gly Lys Leu His Met Met Lys Glu Lys Trp Trp Arg
755                 760                 765                 770
Gly Asn Gly Cys Pro Glu Glu Asp Asn Lys Glu Ala Ser Ala Leu Gly
                775                 780                 785
Val Glu Asn Ile Gly Gly Ile Phe Ile Val Leu Ala Ala Gly Leu Val
            790                 795                 800
Leu Ser Val Phe Val Ala Ile Gly Glu Phe Ile Tyr Lys Ser Arg Lys
            805                 810                 815
Asn Asn Asp Ile Glu Gln Cys Leu Ser Phe Asn Ala Ile Met Glu Glu
            820                 825                 830
Leu Gly Ile Ser Leu Lys Asn Gln Lys Lys Ile Lys Lys Lys Ser Arg
835                 840                 845                 850
Thr Lys Gly Lys Ser Ser Phe Thr Ser Ile Leu Thr Cys His Gln Arg
                855                 860                 865
Arg Thr Gln Arg Lys Glu Thr Val Ala
            870                 875
```

(2) INFORMATION FOR SEQ ID NO:3:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

Ala Ala Phe Leu Thr Val Glu Arg Met Glu Ser Pro Ile Asn Ser Ala

```
            1               5                  10                    15
Asp Asp Leu Ala Lys Gln Thr Lys Ile Glu Tyr Gly Ala Val Arg Asp
                20                  25                  30
Gly Ser Thr Met Thr Phe Phe Lys Lys Ser Lys Ile Ser Thr Tyr Glu
        35                  40                  45
Lys Met
    50
```

(2) INFORMATION FOR SEQ ID NO:4:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Ala Ala Phe Leu Thr Val Glu Arg Met Glu Ser Pro Ile Asp Ser Ala
 1               5                  10                  15
Asp Asp Leu Ala Lys Gln Thr Lys Ile Glu Tyr Gly Ala Val Arg Asp
                20                  25                  30
Gly Ser Thr Met Thr Phe Phe Lys Lys Ser Lys Ile Ser Thr Tyr Glu
        35                  40                  45
Lys Met
    50
```

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GAGAGAATGG AATCCCCCAT AAATTCGGCA GATGATCTGG CAAAGCAAAC        50

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

GAGAGAATGG AATCCCCCAT AGATTCGGCA GATGATCTGG CAAAGCAAAC        50

(2) INFORMATION FOR SEQ ID NO:7:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (v) FRAGMENT TYPE: C-terminal (xi) SEQUENCE DESCRIPTION: SEQ ID NO:7:

Ala Ala Gly Leu Val Leu Ser Val Phe Val Ala Ile Gly Glu Phe Ile
1               5                   10                  15

Tyr Lys Ser Arg Lys Asn Asn Asp Ile Glu Gln Val Ser His Leu Phe
            20                  25                  30

Leu Gly Leu Val Ser Leu
        35

(2) INFORMATION FOR SEQ ID NO:8:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

Ala Ala Gly Leu Val Leu Ser Val Phe Val Ala Ile Gly Glu Phe Ile
1               5                   10                  15

Tyr Lys Ser Arg Lys Asn Asn Asp Ile Glu Gln Cys Leu Ser Phe Asn
            20                  25                  30

Ala Ile Met Glu Glu Leu Gly Ile Ser Leu Lys Asn Gln Lys Lys Ile
        35                  40                  45

Lys Lys
50

(2) INFORMATION FOR SEQ ID NO:9:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

CAAATCACGG AAGAATAATG ATATTGAACA GGTGAGTCAT CTCTTTCTAG GACTGGTTAG    60

TTTATAGTTT GCATTATCTG TCTTAAGTTT GGGGGTTTTT AAGGATGTTT GCTCTTTTT    119

(2) INFORMATION FOR SEQ ID NO:10:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

CAAATCACGG AAGAATAATG ATATTGAACA GTGTCTCTCT TTCAACGCTA TCATGGAAGA    60

ACTGGGAATC TCACTGAAGA ATCAGAAAAA AATAAAGAAA AGTCAAGAA CTAAGGGGAA    120

ATCT    124

(2) INFORMATION FOR SEQ ID NO:11:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (v) FRAGMENT TYPE: N-terminal (ix) FEATURE:
              (A) NAME/KEY: Peptide
              (B) LOCATION: 1..29
              (D) OTHER INFORMATION: /note= "Signal Peptide"

(xi) SEQUENCE DESCRIPTION: SEQ ID NO:11:

```
Met Glu His Gly Thr Leu Leu Ala Gln Pro Gly Leu Trp Thr Arg Asp
1               5                   10                  15

Thr Ser Trp Gly Leu Leu Tyr Phe Leu Cys Tyr Ile Leu Pro Gln Thr
            20                  25                  30

Ala Pro Gln Val Leu Arg Ile Ala Cys Asp Gln Leu
        35                  40
```

(2) INFORMATION FOR SEQ ID NO:12:

(i) SEQUENCE CHARACTERISTICS:
              (A) LENGTH: 100 amino acids
              (B) TYPE: amino acid
              (D) TOPOLOGY: linear (ii) MOLECULE TYPE: peptide (v) FRAGMENT TYPE: N-terminal (ix) FEATURE:
              (A) NAME/KEY: Peptide
              (B) LOCATION: 1..29
              (D) OTHER INFORMATION: /note= "Signal Peptide"

(xi) SEQUENCE DESCRIPTION: SEQ ID NO:12:

```
Met Glu His Gly Thr Leu Leu Ala Gln Pro Gly Leu Trp Thr Arg Asp
1               5                   10                  15

Thr Ser Trp Gly Leu Leu Tyr Phe Leu Cys Tyr Ile Leu Pro Gln Thr
            20                  25                  30

Ala Pro Gln Val Leu Arg Ile Gly Gly Ile Phe Glu Thr Val Glu Asn
        35                  40                  45

Glu Pro Val Asn Val Glu Glu Leu Ala Phe Lys Phe Ala Val Thr Ser
    50                  55                  60

Ile Asn Arg Asn Arg Thr Leu Met Pro Asn Thr Thr Leu Thr Tyr Asp
65                  70                  75                  80

Ile Gln Arg Ile Asn Leu Phe Asp Ser Phe Glu Val Leu Arg Ile Ala
                85                  90                  95

Cys Asp Gln Leu
            100
```

(2) INFORMATION FOR SEQ ID NO:13:

(i) SEQUENCE CHARACTERISTICS:
              (A) LENGTH: 82 base pairs
              (B) TYPE: nucleic acid
              (C) STRANDEDNESS: double
              (D) TOPOLOGY: linear (ii) MOLECULE TYPE: cDNA (xi) SEQUENCE DESCRIPTION: SEQ ID NO:13:

```
ATCCTCCCTC AGACCGCCCC GCAAGTACTC AGGATCGCAT GTGACCAGCT GGCTCTTGGT      60

GTGGCTGCTC TCTTTGGCCC TT                                              82
```

(2) INFORMATION FOR SEQ ID NO:14:

(i) SEQUENCE CHARACTERISTICS:
    (A) LENGTH: 100 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:14:

```
ATCCTCCCTC AGACCGCCCC GCAAGTACTC AGGATCGGAG GGATTTTTGA GAGAGCATGT    60

GACCAGCTGG CTCTTGGTGT GGCTGCTCTC TTTGGCCCTT                         100
```

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:15:

```
ATCGGCGGCA TCTTCATTGT TCTGGCTGCA GGACTCGTGC                          40
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

```
CCATCATTGA GAAGTGGTCC                                                20
```

(2) INFORMATION FOR SEQ ID NO:17:

(i) SEQUENCE CHARACTERISTICS:
        (A) LENGTH: 866 amino acids
        (B) TYPE: amino acid
        (D) TOPOLOGY: linear (ii) MOLECULE TYPE: protein (xi) SEQUENCE DESCRIPTION: SEQ ID NO:17:

```
Met Glu His Gly Thr Leu Leu Ala Gln Pro Gly Leu Trp Thr Arg Asp
-30             -25                 -20                 -15

Thr Ser Trp Ala Leu Leu Tyr Phe Leu Cys Tyr Ile Leu Pro Gln Thr
            -10                  -5                   1

Ala Pro Gln Val Leu Arg Ile Gly Gly Ile Phe Glu Thr Val Glu Asn
             5                  10                  15

Glu Pro Val Asn Val Glu Glu Leu Ala Phe Lys Phe Ala Val Thr Ser
         20                  25                  30

Ile Asn Arg Asn Arg Thr Leu Met Pro Asn Thr Thr Leu Thr Tyr Asp
 35                  40                  45                  50

Ile Gln Arg Ile Asn Leu Phe Asp Ser Phe Glu Ala Ser Arg Arg Ala
                 55                  60                  65

Cys Asp Gln Leu Ala Leu Gly Val Ala Ala Leu Phe Gly Pro Ser His
                 70                  75                  80

Ser Ser Ser Val Ser Ala Val Gln Ser Ile Cys Asn Ala Leu Glu Val
             85                  90                  95

Pro His Ile Gln Thr Arg Trp Lys His Pro Ser Val Asp Asn Lys Asp
        100                 105                 110

Leu Phe Tyr Ile Asn Leu Tyr Pro Asp Tyr Ala Ala Ile Ser Arg Ala
```

```
        115                 120                 125                 130
Ile Leu Asp Leu Val Leu Tyr Tyr Asn Trp Lys Thr Val Thr Val Val
                135                 140                 145

Tyr Glu Asp Ser Thr Gly Leu Ile Arg Leu Gln Glu Leu Ile Lys Ala
            150                 155                 160

Pro Ser Arg Tyr Asn Ile Lys Ile Lys Ile Arg Gln Leu Pro Ser Gly
            165                 170                 175

Asn Lys Asp Ala Lys Pro Leu Leu Lys Glu Met Lys Lys Gly Lys Glu
            180                 185                 190

Phe Tyr Val Ile Phe Asp Cys Ser His Glu Thr Ala Ala Glu Ile Leu
195                 200                 205                 210

Lys Gln Ile Leu Phe Met Gly Met Met Thr Glu Tyr Tyr His Tyr Phe
                215                 220                 225

Phe Thr Thr Leu Asp Leu Phe Ala Leu Asp Leu Glu Leu Tyr Arg Tyr
            230                 235                 240

Ser Gly Val Asn Met Thr Gly Phe Gly Leu Leu Asn Ile Asp Asn Pro
            245                 250                 255

His Val Ser Ser Ile Ile Glu Lys Trp Ser Met Glu Arg Leu Gln Ala
260                 265                 270

Pro Pro Arg Pro Glu Thr Gly Leu Leu Asp Gly Met Met Thr Thr Glu
275                 280                 285                 290

Ala Ala Leu Met Tyr Asp Ala Val Tyr Met Val Ala Ile Ala Ser His
                295                 300                 305

Arg Ala Ser Gln Leu Thr Val Ser Ser Leu Gln Cys His Arg His Lys
            310                 315                 320

Pro Trp Arg Leu Gly Pro Arg Phe Met Asn Leu Ile Lys Glu Ala Arg
            325                 330                 335

Trp Asp Gly Leu Thr Gly His Ile Thr Phe Asn Lys Thr Asn Gly Leu
            340                 345                 350

Arg Lys Asp Phe Asp Leu Asp Ile Ile Ser Leu Lys Glu Glu Gly Thr
355                 360                 365                 370

Glu Lys Ile Gly Ile Trp Asn Ser Asn Ser Gly Leu Asn Met Thr Asp
                375                 380                 385

Ser Asn Lys Asp Lys Ser Ser Asn Ile Thr Asp Ser Leu Ala Asn Arg
            390                 395                 400

Thr Leu Ile Val Thr Thr Ile Leu Glu Glu Pro Tyr Val Met Tyr Arg
            405                 410                 415

Lys Ser Asp Lys Pro Leu Tyr Gly Asn Asp Arg Phe Glu Gly Tyr Cys
            420                 425                 430

Leu Asp Leu Leu Lys Glu Leu Ser Asn Ile Leu Gly Phe Ile Tyr Asp
435                 440                 445                 450

Val Lys Leu Val Pro Asp Gly Lys Tyr Gly Ala Gln Asn Asp Lys Gly
                455                 460                 465

Glu Trp Asn Gly Met Val Lys Glu Leu Ile Asp His Arg Ala Asp Leu
            470                 475                 480

Ala Val Ala Pro Leu Thr Ile Thr Tyr Val Arg Glu Lys Val Ile Asp
            485                 490                 495

Phe Ser Lys Pro Phe Met Thr Leu Gly Ile Ser Ile Leu Tyr Arg Lys
500                 505                 510

Pro Asn Gly Thr Asn Pro Gly Val Phe Ser Phe Leu Asn Pro Leu Ser
515                 520                 525                 530

Pro Asp Ile Trp Met Tyr Val Leu Leu Ala Cys Leu Gly Val Ser Cys
                535                 540                 545
```

```
Val Leu Phe Val Ile Ala Arg Phe Thr Pro Tyr Glu Trp Tyr Asn Pro
                550                 555                 560

His Pro Cys Asn Pro Asp Ser Asp Val Val Glu Asn Asn Phe Thr Leu
        565                 570                 575

Leu Asn Ser Phe Trp Phe Gly Val Gly Ala Leu Met Gln Gln Gly Ser
580                 585                 590

Glu Leu Met Pro Lys Ala Leu Ser Thr Arg Ile Val Gly Gly Ile Trp
595                 600                 605                 610

Trp Phe Phe Thr Leu Ile Ile Ser Ser Tyr Thr Ala Asn Leu Ala
                615                 620                 625

Ala Phe Leu Thr Val Glu Arg Met Glu Ser Pro Ile Asp Ser Ala Asp
                630                 635                 640

Asp Leu Ala Lys Gln Thr Lys Ile Glu Tyr Gly Ala Val Arg Asp Gly
        645                 650                 655

Ser Thr Met Thr Phe Phe Lys Lys Ser Lys Ile Ser Thr Tyr Glu Lys
        660                 665                 670

Met Trp Ala Phe Met Ser Ser Arg Gln Gln Thr Ala Leu Val Arg Asn
675                 680                 685                 690

Ser Asp Glu Gly Ile Gln Arg Val Leu Thr Thr Asp Tyr Ala Leu Leu
                695                 700                 705

Met Glu Ser Thr Ser Ile Glu Tyr Val Thr Gln Arg Asn Cys Asn Leu
                710                 715                 720

Thr Gln Ile Gly Gly Leu Ile Asp Ser Lys Gly Tyr Gly Val Gly Thr
                725                 730                 735

Pro Ile Gly Ser Pro Tyr Arg Asp Lys Ile Thr Ile Ala Ile Leu Gln
        740                 745                 750

Leu Gln Glu Glu Gly Lys Leu His Met Met Lys Glu Lys Trp Trp Arg
755                 760                 765                 770

Gly Asn Gly Cys Pro Glu Glu Asp Asn Lys Glu Ala Ser Ala Leu Gly
                775                 780                 785

Val Glu Asn Ile Gly Gly Ile Phe Ile Val Leu Ala Ala Gly Leu
                790                 795                 800

Val Leu Ser Val Phe Val Ala Ile Gly Glu Phe Ile Tyr Lys Ser Arg
        805                 810                 815

Lys Asn Asn Asp Ile Glu Gln Val Ser His Leu Phe Leu Gly Leu Val
820                 825                 830

Ser Leu
835

(2) INFORMATION FOR SEQ ID NO:18:

(i) SEQUENCE CHARACTERISTICS:
        (A) LENGTH: 849 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Met Glu His Gly Thr Leu Leu Ala Gln Pro Gly Leu Trp Thr Arg Asp
1               5                   10                  15

Thr Ser Trp Ala Leu Leu Tyr Phe Leu Cys Tyr Ile Leu Pro Gln Thr
                20                  25                  30

Ala Pro Gln Ala Ser Arg Arg Ala Cys Asp Gln Leu Ala Leu Gly Val
            35                  40                  45

Ala Ala Leu Phe Gly Pro Ser His Ser Ser Ser Val Ser Ala Val Gln
```

```
                    50                  55                  60
Ser Ile Cys Asn Ala Leu Glu Val Pro His Ile Gln Thr Arg Trp Lys
 65                  70                  75                  80

His Pro Ser Val Asp Asn Lys Asp Leu Phe Tyr Ile Asn Leu Tyr Pro
                 85                  90                  95

Asp Tyr Ala Ala Ile Ser Arg Ala Ile Leu Asp Leu Val Leu Tyr Tyr
            100                 105                 110

Asn Trp Lys Thr Val Thr Val Val Tyr Glu Asp Ser Thr Gly Leu Ile
            115                 120                 125

Arg Leu Gln Glu Leu Ile Lys Ala Pro Ser Arg Tyr Asn Ile Lys Ile
130                 135                 140

Lys Ile Arg Gln Leu Pro Ser Gly Asn Lys Asp Ala Lys Pro Leu Leu
145                 150                 155                 160

Lys Glu Met Lys Lys Gly Lys Glu Phe Tyr Val Ile Phe Asp Cys Ser
            165                 170                 175

His Glu Thr Ala Ala Glu Ile Leu Lys Gln Ile Leu Phe Met Gly Met
            180                 185                 190

Met Thr Glu Tyr Tyr His Tyr Phe Phe Thr Thr Leu Asp Leu Phe Ala
            195                 200                 205

Leu Asp Leu Glu Leu Tyr Arg Tyr Ser Gly Val Asn Met Thr Gly Phe
            210                 215                 220

Gly Leu Leu Asn Ile Asp Asn Pro His Val Ser Ser Ile Ile Glu Lys
225                 230                 235                 240

Trp Ser Met Glu Arg Leu Gln Ala Pro Pro Arg Pro Glu Thr Gly Leu
            245                 250                 255

Leu Asp Gly Met Met Thr Thr Glu Ala Ala Leu Met Tyr Asp Ala Val
            260                 265                 270

Tyr Met Val Ala Ile Ala Ser His Arg Ala Ser Gln Leu Thr Val Ser
            275                 280                 285

Ser Leu Gln Cys His Arg His Lys Pro Trp Arg Leu Gly Pro Arg Phe
290                 295                 300

Met Asn Leu Ile Lys Glu Ala Arg Trp Asp Gly Leu Thr Gly His Ile
305                 310                 315                 320

Thr Phe Asn Lys Thr Asn Gly Leu Arg Lys Asp Phe Asp Leu Asp Ile
            325                 330                 335

Ile Ser Leu Lys Glu Glu Gly Thr Glu Lys Ile Gly Ile Trp Asn Ser
            340                 345                 350

Asn Ser Gly Leu Asn Met Thr Asp Ser Asn Lys Asp Lys Ser Ser Asn
            355                 360                 365

Ile Thr Asp Ser Leu Ala Asn Arg Thr Leu Ile Val Thr Thr Ile Leu
            370                 375                 380

Glu Glu Pro Tyr Val Met Tyr Arg Lys Ser Asp Lys Pro Leu Tyr Gly
385                 390                 395                 400

Asn Asp Arg Phe Glu Gly Tyr Cys Leu Asp Leu Leu Lys Glu Leu Ser
            405                 410                 415

Asn Ile Leu Gly Phe Ile Tyr Asp Val Lys Leu Val Pro Asp Gly Lys
            420                 425                 430

Tyr Gly Ala Gln Asn Asp Lys Gly Glu Trp Asn Gly Met Val Lys Glu
            435                 440                 445

Leu Ile Asp His Arg Ala Asp Leu Ala Val Ala Pro Leu Thr Ile Thr
            450                 455                 460

Tyr Val Arg Glu Lys Val Ile Asp Phe Ser Lys Pro Phe Met Thr Leu
465                 470                 475                 480
```

-continued

```
Gly Ile Ser Ile Leu Tyr Arg Lys Pro Asn Gly Thr Asn Pro Gly Val
                485                 490                 495

Phe Ser Phe Leu Asn Pro Leu Ser Pro Asp Ile Trp Met Tyr Val Leu
                500                 505                 510

Leu Ala Cys Leu Gly Val Ser Cys Val Leu Phe Val Ile Ala Arg Phe
                515                 520                 525

Thr Pro Tyr Glu Trp Tyr Asn Pro His Pro Cys Asn Pro Asp Ser Asp
                530                 535                 540

Val Val Glu Asn Asn Phe Thr Leu Leu Asn Ser Phe Trp Phe Gly Val
545                 550                 555                 560

Gly Ala Leu Met Gln Gln Gly Ser Glu Leu Met Pro Lys Ala Leu Ser
                565                 570                 575

Thr Arg Ile Val Gly Gly Ile Trp Trp Phe Phe Thr Leu Ile Ile Ile
                580                 585                 590

Ser Ser Tyr Thr Ala Asn Leu Ala Ala Phe Leu Thr Val Glu Arg Met
                595                 600                 605

Glu Ser Pro Ile Asp Ser Ala Asp Asp Leu Ala Lys Gln Thr Lys Ile
                610                 615                 620

Glu Tyr Gly Ala Val Arg Asp Gly Ser Thr Met Thr Phe Phe Lys Lys
625                 630                 635                 640

Ser Lys Ile Ser Thr Tyr Glu Lys Met Trp Ala Phe Met Ser Ser Arg
                645                 650                 655

Gln Gln Thr Ala Leu Val Arg Asn Ser Asp Glu Gly Ile Gln Arg Val
                660                 665                 670

Leu Thr Thr Asp Tyr Ala Leu Leu Met Glu Ser Thr Ser Ile Glu Tyr
                675                 680                 685

Val Thr Gln Arg Asn Cys Asn Leu Thr Gln Ile Gly Gly Leu Ile Asp
                690                 695                 700

Ser Lys Gly Tyr Gly Val Gly Thr Pro Ile Gly Ser Pro Tyr Arg Asp
705                 710                 715                 720

Lys Ile Thr Ile Ala Ile Leu Gln Leu Gln Glu Glu Gly Lys Leu His
                725                 730                 735

Met Met Lys Glu Lys Trp Trp Arg Gly Asn Gly Cys Pro Glu Glu Asp
                740                 745                 750

Asn Lys Glu Ala Ser Ala Leu Gly Val Glu Asn Ile Gly Gly Ile Phe
                755                 760                 765

Ile Val Leu Ala Ala Gly Leu Val Leu Ser Val Phe Val Ala Ile Gly
                770                 775                 780

Glu Phe Ile Tyr Lys Ser Arg Lys Asn Asn Asp Ile Glu Gln Cys Leu
785                 790                 795                 800

Ser Phe Asn Ala Ile Met Glu Glu Leu Gly Ile Ser Leu Lys Asn Gln
                805                 810                 815

Lys Lys Ile Lys Lys Lys Ser Arg Thr Lys Gly Lys Ser Ser Phe Thr
                820                 825                 830

Ser Ile Leu Thr Cys His Gln Arg Arg Thr Gln Arg Lys Glu Thr Val
                835                 840                 845

Ala
```